US009579020B2

(12) United States Patent
Libbus et al.

(10) Patent No.: US 9,579,020 B2
(45) Date of Patent: *Feb. 28, 2017

(54) ADHERENT CARDIAC MONITOR WITH ADVANCED SENSING CAPABILITIES

(71) Applicant: Medtronic Monitoring, Inc., San Jose, CA (US)

(72) Inventors: Imad Libbus, Saint Paul, MN (US); Yatheendhar D. Manicka, Woodbury, MN (US); Rich Fogoros, Pittsburgh, PA (US)

(73) Assignee: Medtronic Monitoring, Inc., San Jose, CA (US)

( * ) Notice: Subject to any disclaimer, the term of this patent is extended or adjusted under 35 U.S.C. 154(b) by 900 days.

This patent is subject to a terminal disclaimer.

(21) Appl. No.: 13/902,251

(22) Filed: May 24, 2013

(65) Prior Publication Data

US 2013/0338448 A1 Dec. 19, 2013

Related U.S. Application Data

(62) Division of application No. 12/209,265, filed on Sep. 12, 2008, now Pat. No. 8,460,189.

(Continued)

(51) Int. Cl.
*A61B 5/00* (2006.01)
*A61B 5/0404* (2006.01)
(Continued)

(52) U.S. Cl.
CPC .......... *A61B 5/0006* (2013.01); *A61B 5/0404* (2013.01); *A61B 5/04028* (2013.01);
(Continued)

(58) Field of Classification Search
CPC combination set(s) only.
See application file for complete search history.

(56) References Cited

U.S. PATENT DOCUMENTS

| 834,261 A | 10/1906 | Chambers |
| 2,087,124 A | 7/1937 | Smith et al. |

(Continued)

FOREIGN PATENT DOCUMENTS

| AU | 2003-220574 A8 | 10/2003 |
| EP | 1487535 | 12/2004 |

(Continued)

OTHER PUBLICATIONS

Extended European Search Report for corresponding EP Application No. 08830769.9 mailed on Jun. 18, 2014.

(Continued)

*Primary Examiner* — William Thomson
*Assistant Examiner* — Shirley Jian
(74) *Attorney, Agent, or Firm* — Billion & Armitage; Michael A. Collins

(57) ABSTRACT

An adherent device comprises an adhesive patch with at least two electrodes and an accelerometer. The accelerometer can be used to determine an orientation of the at least two measurement electrodes on a patient. By determining the orientation of the electrodes of the patch on the patient, physiologic measurements with the at least two electrodes can be adjusted and/or corrected in response to the orientation of the patch on the patient. The adherent patch and/or electrodes can be replaced with a second adherent patch and/or electrodes, and the orientation of the second adherent patch and/or electrodes can be determined with the accelerometer or a second accelerometer. The determined orientation of the second patch and/or electrodes on the patient can be used to correct measurements made with the second adherent patch and/or electrodes.

25 Claims, 14 Drawing Sheets

Related U.S. Application Data

(60) Provisional application No. 60/972,537, filed on Sep. 14, 2007, provisional application No. 61/055,666, filed on May 23, 2008, provisional application No. 61/055,662, filed on May 23, 2008.

(51) Int. Cl.
  *A61B 5/053* (2006.01)
  *A61B 5/06* (2006.01)
  *A61B 5/11* (2006.01)
  *A61B 5/0402* (2006.01)
  *G01C 9/06* (2006.01)
  *A61B 5/0408* (2006.01)

(52) U.S. Cl.
  CPC ............ *A61B 5/0537* (2013.01); *A61B 5/061* (2013.01); *A61B 5/11* (2013.01); *A61B 5/4869* (2013.01); *A61B 5/721* (2013.01); *G01C 9/06* (2013.01); *A61B 5/04085* (2013.01); *A61B 5/684* (2013.01); *A61B 5/6823* (2013.01); *A61B 5/6832* (2013.01); *A61B 5/6833* (2013.01); *A61B 2560/0412* (2013.01); *A61B 2562/0219* (2013.01)

(56) References Cited

U.S. PATENT DOCUMENTS

| | | |
|---|---|---|
| 2,184,511 A | 12/1939 | Bagno et al. |
| 3,170,459 A | 2/1965 | Phipps et al. |
| 3,232,291 A | 2/1966 | Parker |
| 3,370,459 A | 2/1968 | Cescati |
| 3,517,999 A | 6/1970 | Weaver |
| 3,620,216 A | 11/1971 | Szymanski |
| 3,677,260 A | 7/1972 | Funfstuck et al. |
| 3,805,769 A | 4/1974 | Sessions |
| 3,845,757 A | 11/1974 | Weyer |
| 3,874,368 A | 4/1975 | Asrican |
| 3,882,853 A | 5/1975 | Gofman et al. |
| 3,942,517 A | 3/1976 | Bowles et al. |
| 3,972,329 A | 8/1976 | Kaufman |
| 4,008,712 A | 2/1977 | Nyboer |
| 4,024,312 A | 5/1977 | Korpman |
| 4,077,406 A | 3/1978 | Sandhage et al. |
| 4,121,573 A | 10/1978 | Crovella et al. |
| 4,141,366 A | 2/1979 | Cross, Jr. et al. |
| RE30,101 E | 9/1979 | Kubicek et al. |
| 4,185,621 A | 1/1980 | Morrow |
| 4,216,462 A | 8/1980 | McGrath et al. |
| 4,300,575 A | 11/1981 | Wilson |
| 4,308,872 A | 1/1982 | Watson et al. |
| 4,358,678 A | 11/1982 | Lawrence |
| 4,409,983 A | 10/1983 | Albert |
| 4,450,527 A | 5/1984 | Sramek |
| 4,451,254 A | 5/1984 | Dinius et al. |
| 4,478,223 A | 10/1984 | Allor |
| 4,498,479 A | 2/1985 | Martio et al. |
| 4,522,211 A | 6/1985 | Bare et al. |
| 4,661,103 A | 4/1987 | Harman |
| 4,664,129 A | 5/1987 | Helzel et al. |
| 4,669,480 A | 6/1987 | Hoffman |
| 4,673,387 A | 6/1987 | Phillips et al. |
| 4,681,118 A | 7/1987 | Asai et al. |
| 4,692,685 A | 9/1987 | Blaze |
| 4,699,146 A | 10/1987 | Sieverding |
| 4,721,110 A | 1/1988 | Lampadius |
| 4,730,611 A | 3/1988 | Lamb |
| 4,733,107 A | 3/1988 | O'Shaughnessy et al. |
| 4,781,200 A | 11/1988 | Baker |
| 4,793,362 A | 12/1988 | Tedner |
| 4,838,273 A | 6/1989 | Cartmell |
| 4,838,279 A | 6/1989 | Fore |
| 4,850,370 A | 7/1989 | Dower |
| 4,880,004 A | 11/1989 | Baker, Jr. et al. |
| 4,895,163 A | 1/1990 | Libke et al. |
| 4,911,175 A | 3/1990 | Shizgal |
| 4,945,916 A | 8/1990 | Kretschmer et al. |
| 4,955,381 A | 9/1990 | Way et al. |
| 4,966,158 A | 10/1990 | Honma et al. |
| 4,981,139 A | 1/1991 | Pfohl |
| 4,988,335 A | 1/1991 | Prindle et al. |
| 4,989,612 A | 2/1991 | Fore |
| 5,001,632 A | 3/1991 | Hall-Tipping |
| 5,012,810 A | 5/1991 | Strand et al. |
| 5,025,791 A | 6/1991 | Niwa |
| 5,027,824 A | 7/1991 | Dougherty et al. |
| 5,050,612 A | 9/1991 | Matsumura |
| 5,063,937 A | 11/1991 | Ezenwa et al. |
| 5,080,099 A | 1/1992 | Way et al. |
| 5,083,563 A | 1/1992 | Collins |
| 5,086,781 A | 2/1992 | Bookspan |
| 5,113,869 A | 5/1992 | Nappholz et al. |
| 5,125,412 A | 6/1992 | Thornton |
| 5,133,355 A | 7/1992 | Strand et al. |
| 5,140,985 A | 8/1992 | Schroeder et al. |
| 5,150,708 A | 9/1992 | Brooks |
| 5,168,874 A | 12/1992 | Segalowitz |
| 5,226,417 A | 7/1993 | Swedlow et al. |
| 5,241,300 A | 8/1993 | Buschmann |
| 5,257,627 A | 11/1993 | Rapoport |
| 5,271,411 A | 12/1993 | Ripley et al. |
| 5,273,532 A | 12/1993 | Niezink et al. |
| 5,282,840 A | 2/1994 | Hudrlik |
| 5,291,013 A | 3/1994 | Nafarrate et al. |
| 5,297,556 A | 3/1994 | Shankar |
| 5,301,677 A | 4/1994 | Hsung |
| 5,319,363 A | 6/1994 | Welch et al. |
| 5,331,966 A | 7/1994 | Bennett et al. |
| 5,335,664 A | 8/1994 | Nagashima |
| 5,343,869 A | 9/1994 | Pross et al. |
| 5,353,793 A | 10/1994 | Bornn |
| 5,362,069 A | 11/1994 | Hall-Tipping |
| 5,375,604 A | 12/1994 | Kelly et al. |
| 5,411,530 A | 5/1995 | Akhtar |
| 5,437,285 A | 8/1995 | Verrier et al. |
| 5,443,073 A | 8/1995 | Wang et al. |
| 5,449,000 A | 9/1995 | Libke et al. |
| 5,450,845 A | 9/1995 | Axelgaard |
| 5,454,377 A | 10/1995 | Dzwonczyk et al. |
| 5,464,012 A | 11/1995 | Falcone |
| 5,469,859 A | 11/1995 | Tsoglin et al. |
| 5,482,036 A | 1/1996 | Diab et al. |
| 5,496,361 A | 3/1996 | Moberg et al. |
| 5,503,157 A | 4/1996 | Sramek |
| 5,511,548 A | 4/1996 | Riazzi et al. |
| 5,511,553 A | 4/1996 | Segalowitz |
| 5,518,001 A | 5/1996 | Snell |
| 5,523,742 A | 6/1996 | Simkins et al. |
| 5,529,072 A | 6/1996 | Sramek |
| 5,544,661 A | 8/1996 | Davis et al. |
| 5,558,638 A | 9/1996 | Evers et al. |
| 5,560,368 A | 10/1996 | Berger |
| 5,564,429 A | 10/1996 | Bornn et al. |
| 5,564,434 A | 10/1996 | Halperin et al. |
| 5,566,671 A | 10/1996 | Lyons |
| 5,575,284 A | 11/1996 | Athan et al. |
| 5,607,454 A | 3/1997 | Cameron et al. |
| 5,632,272 A | 5/1997 | Diab et al. |
| 5,634,468 A | 6/1997 | Platt et al. |
| 5,642,734 A | 7/1997 | Ruben et al. |
| 5,673,704 A | 10/1997 | Marchlinski et al. |
| 5,678,562 A | 10/1997 | Sellers |
| 5,687,717 A | 11/1997 | Halpern et al. |
| 5,710,376 A | 1/1998 | Weber, Jr. |
| 5,718,234 A | 2/1998 | Warden et al. |
| 5,724,025 A | 3/1998 | Tavori |
| 5,738,107 A | 4/1998 | Martinsen et al. |
| 5,748,103 A | 5/1998 | Flach et al. |
| 5,767,791 A | 6/1998 | Stoop et al. |
| 5,769,793 A | 6/1998 | Pincus et al. |
| 5,772,508 A | 6/1998 | Sugita et al. |
| 5,772,586 A | 6/1998 | Heinonen et al. |
| 5,778,882 A | 7/1998 | Raymond et al. |
| 5,788,643 A | 8/1998 | Feldman |

(56) References Cited

U.S. PATENT DOCUMENTS

| | | | |
|---|---|---|---|
| 5,788,682 A | 8/1998 | Maget | |
| 5,803,915 A | 9/1998 | Kremenchugsky et al. | |
| 5,807,272 A | 9/1998 | Kun | |
| 5,814,079 A | 9/1998 | Kieval et al. | |
| 5,817,035 A | 10/1998 | Sullivan | |
| 5,833,603 A | 11/1998 | Kovacs et al. | |
| 5,836,990 A | 11/1998 | Li | |
| 5,855,614 A | 1/1999 | Stevens et al. | |
| 5,860,860 A | 1/1999 | Clayman | |
| 5,862,802 A | 1/1999 | Bird | |
| 5,862,803 A | 1/1999 | Besson et al. | |
| 5,865,733 A | 2/1999 | Malinouskas et al. | |
| 5,876,353 A | 3/1999 | Riff | |
| 5,904,708 A | 5/1999 | Goedeke | |
| 5,935,079 A | 8/1999 | Swanson et al. | |
| 5,941,831 A | 8/1999 | Turcott | |
| 5,944,659 A | 8/1999 | Flach et al. | |
| 5,949,636 A | 9/1999 | Johnson et al. | |
| 5,957,854 A | 9/1999 | Besson et al. | |
| 5,957,861 A | 9/1999 | Combs et al. | |
| 5,964,703 A | 10/1999 | Goodman et al. | |
| 5,970,986 A | 10/1999 | Bolz et al. | |
| 5,984,102 A | 11/1999 | Tay | |
| 5,987,352 A | 11/1999 | Klein et al. | |
| 6,007,532 A | 12/1999 | Netherly | |
| 6,027,523 A | 2/2000 | Schmieding | |
| 6,045,513 A | 4/2000 | Stone et al. | |
| 6,047,203 A | 4/2000 | Sackner et al. | |
| 6,047,259 A | 4/2000 | Campbell et al. | |
| 6,049,730 A | 4/2000 | Kristbjarnarson | |
| 6,050,267 A | 4/2000 | Nardella et al. | |
| 6,050,951 A | 4/2000 | Friedman et al. | |
| 6,052,615 A | 4/2000 | Feild et al. | |
| 6,067,467 A | 5/2000 | John | |
| 6,080,106 A | 6/2000 | Lloyd et al. | |
| 6,081,735 A | 6/2000 | Diab et al. | |
| 6,095,991 A | 8/2000 | Krausman et al. | |
| 6,102,856 A | 8/2000 | Groff et al. | |
| 6,104,949 A | 8/2000 | Pitts Crick et al. | |
| 6,112,224 A | 8/2000 | Peifer et al. | |
| 6,117,077 A | 9/2000 | Del Mar et al. | |
| 6,125,297 A | 9/2000 | Siconolfi | |
| 6,129,744 A | 10/2000 | Boute | |
| 6,141,575 A | 10/2000 | Price | |
| 6,144,878 A | 11/2000 | Schroeppel et al. | |
| 6,164,284 A | 12/2000 | Schulman et al. | |
| 6,181,963 B1 | 1/2001 | Chin et al. | |
| 6,185,452 B1 | 2/2001 | Schulman et al. | |
| 6,190,313 B1 | 2/2001 | Hinkle | |
| 6,190,324 B1 | 2/2001 | Kieval et al. | |
| 6,198,394 B1 | 3/2001 | Jacobsen et al. | |
| 6,198,955 B1 | 3/2001 | Axelgaard et al. | |
| 6,208,894 B1 | 3/2001 | Schulman et al. | |
| 6,212,427 B1 | 4/2001 | Hoover | |
| 6,213,942 B1 | 4/2001 | Flach et al. | |
| 6,225,901 B1 | 5/2001 | Kail, IV | |
| 6,245,021 B1 | 6/2001 | Stampfer | |
| 6,259,939 B1 | 7/2001 | Rogel | |
| 6,267,730 B1 | 7/2001 | Pacunas | |
| 6,272,377 B1 | 8/2001 | Sweeney et al. | |
| 6,277,078 B1 | 8/2001 | Porat et al. | |
| 6,287,252 B1 | 9/2001 | Lugo | |
| 6,289,238 B1 | 9/2001 | Besson et al. | |
| 6,290,646 B1 | 9/2001 | Cosentino et al. | |
| 6,295,466 B1 | 9/2001 | Ishikawa et al. | |
| 6,305,943 B1 | 10/2001 | Pougatchev et al. | |
| 6,306,088 B1 | 10/2001 | Krausman et al. | |
| 6,308,094 B1 | 10/2001 | Shusterman et al. | |
| 6,312,378 B1 | 11/2001 | Bardy | |
| 6,315,721 B2 | 11/2001 | Schulman et al. | |
| 6,327,487 B1 | 12/2001 | Stratbucker | |
| 6,330,464 B1 | 12/2001 | Colvin et al. | |
| 6,336,903 B1 | 1/2002 | Bardy | |
| 6,339,722 B1 | 1/2002 | Heethaar et al. | |
| 6,343,140 B1 | 1/2002 | Brooks | |
| 6,347,245 B1 | 2/2002 | Lee et al. | |
| 6,358,208 B1 | 3/2002 | Lang et al. | |
| 6,385,473 B1 | 5/2002 | Haines et al. | |
| 6,398,727 B1 | 6/2002 | Bui et al. | |
| 6,400,982 B2 | 6/2002 | Sweeney et al. | |
| 6,409,674 B1 | 6/2002 | Brockway et al. | |
| 6,411,853 B1 | 6/2002 | Millot et al. | |
| 6,416,471 B1 | 7/2002 | Kumar et al. | |
| 6,440,069 B1 | 8/2002 | Raymond et al. | |
| 6,442,422 B1 | 8/2002 | Duckert | |
| 6,450,820 B1 | 9/2002 | Palsson et al. | |
| 6,450,953 B1 | 9/2002 | Place et al. | |
| 6,453,186 B1 | 9/2002 | Lovejoy et al. | |
| 6,454,707 B1 | 9/2002 | Casscells, III et al. | |
| 6,454,708 B1 | 9/2002 | Ferguson et al. | |
| 6,459,930 B1 | 10/2002 | Takehara et al. | |
| 6,463,328 B1 | 10/2002 | John | |
| 6,473,640 B1 | 10/2002 | Erlebacher | |
| 6,480,733 B1 | 11/2002 | Turcott | |
| 6,480,734 B1 | 11/2002 | Zhang et al. | |
| 6,485,461 B1 | 11/2002 | Mason et al. | |
| 6,490,478 B1 | 12/2002 | Zhang et al. | |
| 6,491,647 B1 | 12/2002 | Bridger et al. | |
| 6,494,829 B1 | 12/2002 | New, Jr. et al. | |
| 6,496,715 B1 | 12/2002 | Lee et al. | |
| 6,512,949 B1 | 1/2003 | Combs et al. | |
| 6,520,967 B1 | 2/2003 | Cauthen | |
| 6,527,711 B1 | 3/2003 | Stivoric et al. | |
| 6,527,729 B1 | 3/2003 | Turcott | |
| 6,528,960 B1 | 3/2003 | Roden et al. | |
| 6,544,173 B2 | 4/2003 | West et al. | |
| 6,544,174 B2 | 4/2003 | West et al. | |
| 6,551,251 B2 | 4/2003 | Zuckerwar et al. | |
| 6,551,252 B2 | 4/2003 | Sackner et al. | |
| 6,569,160 B1 | 5/2003 | Goldin et al. | |
| 6,572,557 B2 | 6/2003 | Tchou et al. | |
| 6,572,636 B1 | 6/2003 | Hagen et al. | |
| 6,577,139 B2 | 6/2003 | Cooper | |
| 6,577,893 B1 | 6/2003 | Besson et al. | |
| 6,577,897 B1 | 6/2003 | Shurubura et al. | |
| 6,579,231 B1 | 6/2003 | Phipps | |
| 6,580,942 B1 | 6/2003 | Willshire | |
| 6,584,343 B1 | 6/2003 | Ransbury et al. | |
| 6,587,715 B2 | 7/2003 | Singer | |
| 6,589,170 B1 | 7/2003 | Flach et al. | |
| 6,595,927 B2 | 7/2003 | Pitts-Crick et al. | |
| 6,595,929 B2 | 7/2003 | Stivoric et al. | |
| 6,600,949 B1 | 7/2003 | Turcott | |
| 6,602,201 B1 | 8/2003 | Hepp et al. | |
| 6,605,038 B1 | 8/2003 | Teller et al. | |
| 6,611,705 B2 | 8/2003 | Hopman et al. | |
| 6,611,783 B2 * | 8/2003 | Kelly, Jr. | A61B 5/0002 340/573.1 |
| 6,616,606 B1 | 9/2003 | Petersen et al. | |
| 6,622,042 B1 | 9/2003 | Thacker | |
| 6,636,754 B1 | 10/2003 | Baura et al. | |
| 6,641,542 B2 | 11/2003 | Cho et al. | |
| 6,645,153 B2 | 11/2003 | Kroll et al. | |
| 6,649,829 B2 | 11/2003 | Garber et al. | |
| 6,650,917 B2 | 11/2003 | Diab et al. | |
| 6,658,300 B2 | 12/2003 | Govari et al. | |
| 6,659,947 B1 | 12/2003 | Carter et al. | |
| 6,659,949 B1 | 12/2003 | Lang et al. | |
| 6,687,540 B2 | 2/2004 | Marcovecchio | |
| 6,697,658 B2 | 2/2004 | Al-Ali | |
| RE38,476 E | 3/2004 | Diab et al. | |
| 6,699,200 B2 | 3/2004 | Cao et al. | |
| 6,701,271 B2 | 3/2004 | Willner et al. | |
| 6,714,813 B2 | 3/2004 | Ishigooka et al. | |
| RE38,492 E | 4/2004 | Diab et al. | |
| 6,721,594 B2 | 4/2004 | Conley et al. | |
| 6,728,572 B2 | 4/2004 | Hsu et al. | |
| 6,748,269 B2 | 6/2004 | Thompson et al. | |
| 6,749,566 B2 | 6/2004 | Russ | |
| 6,751,498 B1 | 6/2004 | Greenberg et al. | |
| 6,760,617 B2 | 7/2004 | Ward et al. | |
| 6,773,396 B2 | 8/2004 | Flach et al. | |
| 6,775,566 B2 | 8/2004 | Nissila | |
| 6,790,178 B1 | 9/2004 | Mault et al. | |

(56) References Cited

U.S. PATENT DOCUMENTS

| | | |
|---|---|---|
| 6,795,722 B2 | 9/2004 | Sheraton et al. |
| 6,814,706 B2 | 11/2004 | Barton et al. |
| 6,816,744 B2 | 11/2004 | Garfield et al. |
| 6,819,956 B2 | 11/2004 | DiLorenzo |
| 6,821,249 B2 | 11/2004 | Casscells, III et al. |
| 6,824,515 B2 | 11/2004 | Suorsa et al. |
| 6,827,690 B2 | 12/2004 | Bardy |
| 6,829,503 B2 | 12/2004 | Alt |
| 6,858,006 B2 | 2/2005 | MacCarter et al. |
| 6,871,211 B2 | 3/2005 | Labounty et al. |
| 6,878,121 B2 | 4/2005 | Krausman et al. |
| 6,879,850 B2 | 4/2005 | Kimball |
| 6,881,191 B2 * | 4/2005 | Oakley ............... A61B 5/0006 600/391 |
| 6,887,201 B2 | 5/2005 | Bardy |
| 6,890,096 B2 | 5/2005 | Tokita et al. |
| 6,893,396 B2 | 5/2005 | Schulze et al. |
| 6,894,204 B2 | 5/2005 | Dunshee |
| 6,906,530 B2 | 6/2005 | Geisel |
| 6,912,414 B2 | 6/2005 | Tong |
| 6,936,006 B2 | 8/2005 | Sabra |
| 6,940,403 B2 | 9/2005 | Kail, IV |
| 6,942,622 B1 | 9/2005 | Turcott |
| 6,952,695 B1 | 10/2005 | Trinks et al. |
| 6,970,742 B2 | 11/2005 | Mann et al. |
| 6,972,683 B2 | 12/2005 | Lestienne et al. |
| 6,978,177 B1 | 12/2005 | Chen et al. |
| 6,980,851 B2 | 12/2005 | Zhu et al. |
| 6,980,852 B2 | 12/2005 | Jersey-Willuhn et al. |
| 6,985,078 B2 | 1/2006 | Suzuki et al. |
| 6,987,965 B2 | 1/2006 | Ng et al. |
| 6,988,989 B2 | 1/2006 | Weiner et al. |
| 6,993,378 B2 | 1/2006 | Wiederhold et al. |
| 6,997,879 B1 | 2/2006 | Turcott |
| 7,003,346 B2 | 2/2006 | Singer |
| 7,009,362 B2 | 3/2006 | Tsukamoto et al. |
| 7,010,340 B2 | 3/2006 | Scarantino et al. |
| 7,018,338 B2 | 3/2006 | Vetter et al. |
| 7,020,508 B2 | 3/2006 | Stivoric et al. |
| 7,027,862 B2 | 4/2006 | Dahl et al. |
| 7,041,062 B2 | 5/2006 | Friedrichs et al. |
| 7,044,911 B2 | 5/2006 | Drinan et al. |
| 7,047,067 B2 | 5/2006 | Gray et al. |
| 7,050,846 B2 | 5/2006 | Sweeney et al. |
| 7,054,679 B2 | 5/2006 | Hirsh |
| 7,059,767 B2 | 6/2006 | Tokita et al. |
| 7,088,242 B2 | 8/2006 | Aupperle et al. |
| 7,113,826 B2 | 9/2006 | Henry et al. |
| 7,118,531 B2 | 10/2006 | Krill |
| 7,127,370 B2 | 10/2006 | Kelly, Jr. et al. |
| 7,129,836 B2 | 10/2006 | Lawson et al. |
| 7,130,396 B2 | 10/2006 | Rogers et al. |
| 7,130,679 B2 | 10/2006 | Parsonnet et al. |
| 7,133,716 B2 | 11/2006 | Kraemer et al. |
| 7,136,697 B2 | 11/2006 | Singer |
| 7,136,703 B1 | 11/2006 | Cappa et al. |
| 7,142,907 B2 | 11/2006 | Xue et al. |
| 7,149,574 B2 | 12/2006 | Yun et al. |
| 7,149,773 B2 | 12/2006 | Haller et al. |
| 7,153,262 B2 | 12/2006 | Stivoric et al. |
| 7,156,807 B2 | 1/2007 | Carter et al. |
| 7,156,808 B2 | 1/2007 | Quy |
| 7,160,252 B2 | 1/2007 | Cho et al. |
| 7,160,253 B2 | 1/2007 | Nissila |
| 7,166,063 B2 | 1/2007 | Rahman et al. |
| 7,167,743 B2 | 1/2007 | Heruth et al. |
| 7,184,821 B2 | 2/2007 | Belalcazar et al. |
| 7,191,000 B2 | 3/2007 | Zhu et al. |
| 7,194,306 B1 | 3/2007 | Turcott |
| 7,206,630 B1 | 4/2007 | Tarler |
| 7,209,787 B2 | 4/2007 | DiLorenzo |
| 7,212,849 B2 | 5/2007 | Zhang et al. |
| 7,215,984 B2 | 5/2007 | Diab et al. |
| 7,215,991 B2 | 5/2007 | Besson et al. |
| 7,231,254 B2 | 6/2007 | DiLorenzo |
| 7,238,159 B2 | 7/2007 | Banet et al. |
| 7,248,916 B2 | 7/2007 | Bardy |
| 7,251,524 B1 | 7/2007 | Hepp et al. |
| 7,257,438 B2 | 8/2007 | Kinast |
| 7,261,690 B2 | 8/2007 | Teller et al. |
| 7,277,741 B2 | 10/2007 | Debreczeny et al. |
| 7,284,904 B2 | 10/2007 | Tokita et al. |
| 7,285,090 B2 | 10/2007 | Stivoric et al. |
| 7,294,105 B1 | 11/2007 | Islam |
| 7,295,879 B2 | 11/2007 | Denker et al. |
| 7,297,119 B2 | 11/2007 | Westbrook et al. |
| 7,318,808 B2 | 1/2008 | Tarassenko et al. |
| 7,319,386 B2 | 1/2008 | Collins, Jr. et al. |
| 7,324,851 B1 | 1/2008 | DiLorenzo |
| 7,336,187 B2 | 2/2008 | Hubbard, Jr. et al. |
| 7,346,380 B2 | 3/2008 | Axelgaard et al. |
| 7,382,247 B2 | 6/2008 | Welch et al. |
| 7,384,398 B2 | 6/2008 | Gagnadre et al. |
| 7,390,299 B2 | 6/2008 | Weiner et al. |
| 7,395,106 B2 | 7/2008 | Ryu et al. |
| 7,423,526 B2 | 9/2008 | Despotis |
| 7,423,537 B2 | 9/2008 | Bonnet et al. |
| 7,443,302 B2 | 10/2008 | Reeder et al. |
| 7,450,024 B2 | 11/2008 | Wildman et al. |
| 7,468,032 B2 | 12/2008 | Stahmann et al. |
| 7,510,699 B2 | 3/2009 | Black et al. |
| 7,660,632 B2 | 2/2010 | Kirby et al. |
| 7,701,227 B2 | 4/2010 | Saulnier et al. |
| 7,813,778 B2 | 10/2010 | Benaron et al. |
| 7,881,763 B2 | 2/2011 | Brauker et al. |
| 7,942,824 B1 | 5/2011 | Kayyali et al. |
| 8,249,686 B2 | 8/2012 | Libbus et al. |
| 8,285,356 B2 | 10/2012 | Bly et al. |
| 8,795,174 B2 * | 8/2014 | Manicka ............... A61B 5/4875 600/301 |
| 9,101,285 B2 * | 8/2015 | Markowitz ........... A61B 5/0422 |
| 9,113,807 B2 * | 8/2015 | Koyrakh ............... A61B 5/053 |
| 9,345,414 B1 * | 5/2016 | Bardy ................. A61B 5/04017 |
| 9,364,155 B2 * | 6/2016 | Bardy ................. A61B 5/02055 |
| 2001/0047127 A1 | 11/2001 | New, Jr. et al. |
| 2002/0004640 A1 | 1/2002 | Conn et al. |
| 2002/0019586 A1 | 2/2002 | Teller et al. |
| 2002/0019588 A1 | 2/2002 | Marro et al. |
| 2002/0022786 A1 | 2/2002 | Takehara et al. |
| 2002/0028989 A1 | 3/2002 | Pelletier et al. |
| 2002/0032581 A1 | 3/2002 | Reitberg |
| 2002/0045836 A1 | 4/2002 | Alkawwas |
| 2002/0088465 A1 | 7/2002 | Hill |
| 2002/0099277 A1 | 7/2002 | Harry et al. |
| 2002/0116009 A1 | 8/2002 | Fraser et al. |
| 2002/0123672 A1 | 9/2002 | Christophersom et al. |
| 2002/0123674 A1 | 9/2002 | Plicchi et al. |
| 2002/0138017 A1 | 9/2002 | Bui et al. |
| 2002/0167389 A1 | 11/2002 | Uchikoba et al. |
| 2002/0182485 A1 | 12/2002 | Anderson et al. |
| 2003/0009092 A1 | 1/2003 | Parker |
| 2003/0023184 A1 | 1/2003 | Pitts-Crick et al. |
| 2003/0028221 A1 | 2/2003 | Zhu et al. |
| 2003/0028327 A1 | 2/2003 | Brunner et al. |
| 2003/0045922 A1 | 3/2003 | Northrop |
| 2003/0051144 A1 | 3/2003 | Williams |
| 2003/0055460 A1 | 3/2003 | Owen et al. |
| 2003/0083581 A1 | 5/2003 | Taha et al. |
| 2003/0085717 A1 | 5/2003 | Cooper |
| 2003/0087244 A1 | 5/2003 | McCarthy |
| 2003/0092975 A1 | 5/2003 | Casscells, III et al. |
| 2003/0093125 A1 | 5/2003 | Zhu et al. |
| 2003/0093298 A1 | 5/2003 | Hernandez et al. |
| 2003/0100367 A1 | 5/2003 | Cooke |
| 2003/0105411 A1 | 6/2003 | Smallwood et al. |
| 2003/0135127 A1 | 7/2003 | Sackner et al. |
| 2003/0143544 A1 | 7/2003 | McCarthy |
| 2003/0149349 A1 | 8/2003 | Jensen |
| 2003/0181815 A1 | 9/2003 | Ebner et al. |
| 2003/0187370 A1 | 10/2003 | Kodama |
| 2003/0191503 A1 | 10/2003 | Zhu et al. |
| 2003/0212319 A1 | 11/2003 | Magill |
| 2003/0221687 A1 | 12/2003 | Kaigler |
| 2003/0233129 A1 | 12/2003 | Matos |

(56) References Cited

U.S. PATENT DOCUMENTS

| | | |
|---|---|---|
| 2004/0006279 A1 | 1/2004 | Arad (Abboud) |
| 2004/0010303 A1 | 1/2004 | Bolea et al. |
| 2004/0014422 A1 | 1/2004 | Kallio |
| 2004/0015058 A1 | 1/2004 | Besson et al. |
| 2004/0019292 A1 | 1/2004 | Drinan et al. |
| 2004/0044293 A1 | 3/2004 | Burton |
| 2004/0049132 A1 | 3/2004 | Barron et al. |
| 2004/0064133 A1 | 4/2004 | Miller et al. |
| 2004/0073094 A1 | 4/2004 | Baker |
| 2004/0073126 A1 | 4/2004 | Rowlandson |
| 2004/0077954 A1* | 4/2004 | Oakley ............... A61B 5/0006 600/483 |
| 2004/100376 A1 | 5/2004 | Lye et al. |
| 2004/0102683 A1 | 5/2004 | Khanuja et al. |
| 2004/0106951 A1 | 6/2004 | Edman et al. |
| 2004/0122489 A1 | 6/2004 | Mazar et al. |
| 2004/0127790 A1 | 7/2004 | Lang et al. |
| 2004/0133079 A1 | 7/2004 | Mazar et al. |
| 2004/0133081 A1 | 7/2004 | Teller et al. |
| 2004/0134496 A1 | 7/2004 | Cho et al. |
| 2004/0143170 A1 | 7/2004 | DuRousseau |
| 2004/0147969 A1 | 7/2004 | Mann et al. |
| 2004/0152956 A1 | 8/2004 | Korman |
| 2004/0158132 A1 | 8/2004 | Zaleski |
| 2004/0167389 A1 | 8/2004 | Brabrand |
| 2004/0172080 A1 | 9/2004 | Stadler et al. |
| 2004/0199056 A1 | 10/2004 | Husemann et al. |
| 2004/0215240 A1 | 10/2004 | Lovett et al. |
| 2004/0215247 A1 | 10/2004 | Bolz |
| 2004/0220639 A1 | 11/2004 | Mulligan et al. |
| 2004/0225199 A1 | 11/2004 | Evanyk et al. |
| 2004/0225203 A1 | 11/2004 | Jemison et al. |
| 2004/0243018 A1 | 12/2004 | Organ et al. |
| 2004/0267142 A1 | 12/2004 | Paul |
| 2005/0004506 A1 | 1/2005 | Gyory |
| 2005/0015094 A1 | 1/2005 | Keller |
| 2005/0015095 A1 | 1/2005 | Keller |
| 2005/0020935 A1 | 1/2005 | Helzel et al. |
| 2005/0027175 A1 | 2/2005 | Yang |
| 2005/0027204 A1 | 2/2005 | Kligfield et al. |
| 2005/0027207 A1 | 2/2005 | Westbrook et al. |
| 2005/0027918 A1 | 2/2005 | Govindarajulu et al. |
| 2005/0043675 A1 | 2/2005 | Pastore et al. |
| 2005/0054944 A1 | 3/2005 | Nakada et al. |
| 2005/0059867 A1 | 3/2005 | Chung |
| 2005/0065445 A1 | 3/2005 | Arzbaecher et al. |
| 2005/0065571 A1 | 3/2005 | Imran |
| 2005/0070768 A1 | 3/2005 | Zhu et al. |
| 2005/0070778 A1 | 3/2005 | Lackey et al. |
| 2005/0080346 A1 | 4/2005 | Gianchandani et al. |
| 2005/0080460 A1 | 4/2005 | Wang et al. |
| 2005/0080463 A1 | 4/2005 | Stahmann et al. |
| 2005/0085734 A1 | 4/2005 | Tehrani |
| 2005/0091338 A1 | 4/2005 | de la Huerga |
| 2005/0096513 A1 | 5/2005 | Ozguz et al. |
| 2005/0113703 A1 | 5/2005 | Farringdon et al. |
| 2005/0124878 A1 | 6/2005 | Sharony |
| 2005/0124901 A1 | 6/2005 | Misczynski et al. |
| 2005/0124908 A1 | 6/2005 | Belalcazar et al. |
| 2005/0131288 A1 | 6/2005 | Turner et al. |
| 2005/0137464 A1 | 6/2005 | Bomba |
| 2005/0137626 A1 | 6/2005 | Pastore et al. |
| 2005/0148895 A1 | 7/2005 | Misczynski et al. |
| 2005/0158539 A1 | 7/2005 | Murphy et al. |
| 2005/0177038 A1 | 8/2005 | Kolpin et al. |
| 2005/0187482 A1 | 8/2005 | O'Brien et al. |
| 2005/0187796 A1 | 8/2005 | Rosenfeld et al. |
| 2005/0192488 A1 | 9/2005 | Bryenton et al. |
| 2005/0197654 A1 | 9/2005 | Edman et al. |
| 2005/0203433 A1 | 9/2005 | Singer |
| 2005/0203435 A1 | 9/2005 | Nakada |
| 2005/0203436 A1 | 9/2005 | Davies |
| 2005/0203637 A1 | 9/2005 | Edman et al. |
| 2005/0206518 A1 | 9/2005 | Welch et al. |
| 2005/0215914 A1 | 9/2005 | Bornzin et al. |
| 2005/0215918 A1 | 9/2005 | Frantz et al. |
| 2005/0228234 A1 | 10/2005 | Yang |
| 2005/0228238 A1 | 10/2005 | Monitzer |
| 2005/0228244 A1 | 10/2005 | Banet |
| 2005/0239493 A1 | 10/2005 | Batkin et al. |
| 2005/0240087 A1 | 10/2005 | Keenan et al. |
| 2005/0251044 A1 | 11/2005 | Hoctor et al. |
| 2005/0256418 A1 | 11/2005 | Mietus et al. |
| 2005/0261598 A1 | 11/2005 | Banet et al. |
| 2005/0261743 A1 | 11/2005 | Kroll |
| 2005/0267376 A1 | 12/2005 | Marossero et al. |
| 2005/0267377 A1 | 12/2005 | Marossero et al. |
| 2005/0267381 A1 | 12/2005 | Benditt et al. |
| 2005/0273023 A1 | 12/2005 | Bystrom et al. |
| 2005/0277841 A1 | 12/2005 | Shennib |
| 2005/0277842 A1 | 12/2005 | Silva |
| 2005/0277992 A1 | 12/2005 | Koh et al. |
| 2005/0280531 A1 | 12/2005 | Fadem et al. |
| 2005/0283197 A1 | 12/2005 | Daum et al. |
| 2005/0288600 A1 | 12/2005 | Zhang et al. |
| 2005/0288601 A1 | 12/2005 | Wood et al. |
| 2006/0004300 A1 | 1/2006 | Kennedy |
| 2006/0004377 A1 | 1/2006 | Keller |
| 2006/0009697 A1 | 1/2006 | Banet et al. |
| 2006/0009701 A1 | 1/2006 | Nissila et al. |
| 2006/0010090 A1 | 1/2006 | Brockway et al. |
| 2006/0020218 A1 | 1/2006 | Freeman et al. |
| 2006/0025661 A1 | 2/2006 | Sweeney et al. |
| 2006/0030781 A1 | 2/2006 | Shennib |
| 2006/0030782 A1 | 2/2006 | Shennib |
| 2006/0031102 A1 | 2/2006 | Teller et al. |
| 2006/0041280 A1 | 2/2006 | Stahmann et al. |
| 2006/0047215 A1 | 3/2006 | Newman et al. |
| 2006/0052678 A1 | 3/2006 | Drinan et al. |
| 2006/0058543 A1 | 3/2006 | Walter et al. |
| 2006/0058593 A1 | 3/2006 | Drinan et al. |
| 2006/0064030 A1 | 3/2006 | Cosentino et al. |
| 2006/0064040 A1 | 3/2006 | Berger et al. |
| 2006/0064142 A1 | 3/2006 | Chavan et al. |
| 2006/0066449 A1 | 3/2006 | Johnson |
| 2006/0074283 A1 | 4/2006 | Henderson et al. |
| 2006/0074462 A1 | 4/2006 | Verhoef |
| 2006/0075257 A1 | 4/2006 | Martis et al. |
| 2006/0084881 A1 | 4/2006 | Korzinov et al. |
| 2006/0085049 A1 | 4/2006 | Cory et al. |
| 2006/0089679 A1 | 4/2006 | Zhu et al. |
| 2006/0094948 A1 | 5/2006 | Gough et al. |
| 2006/0102476 A1 | 5/2006 | Niwa et al. |
| 2006/0116592 A1 | 6/2006 | Zhou et al. |
| 2006/0122474 A1 | 6/2006 | Teller et al. |
| 2006/0135858 A1 | 6/2006 | Nidd et al. |
| 2006/0142654 A1 | 6/2006 | Rytky |
| 2006/0142820 A1 | 6/2006 | Von Arx et al. |
| 2006/0149168 A1 | 7/2006 | Czarnek |
| 2006/0155174 A1 | 7/2006 | Glukhovsky et al. |
| 2006/0155183 A1 | 7/2006 | Kroecker et al. |
| 2006/0155200 A1 | 7/2006 | Ng |
| 2006/0157893 A1 | 7/2006 | Patel |
| 2006/0161073 A1 | 7/2006 | Singer |
| 2006/0161205 A1 | 7/2006 | Mitrani et al. |
| 2006/0161459 A9 | 7/2006 | Rosenfeld et al. |
| 2006/0167374 A1 | 7/2006 | Takehara et al. |
| 2006/0173257 A1 | 8/2006 | Nagai et al. |
| 2006/0173269 A1 | 8/2006 | Glossop |
| 2006/0195020 A1 | 8/2006 | Martin et al. |
| 2006/0195039 A1 | 8/2006 | Drew et al. |
| 2006/0195097 A1 | 8/2006 | Evans et al. |
| 2006/0195144 A1 | 8/2006 | Giftakis et al. |
| 2006/0202816 A1 | 9/2006 | Crump et al. |
| 2006/0212097 A1 | 9/2006 | Varadan et al. |
| 2006/0224051 A1 | 10/2006 | Teller et al. |
| 2006/0224072 A1 | 10/2006 | Shennib |
| 2006/0224079 A1 | 10/2006 | Washchuk |
| 2006/0235281 A1 | 10/2006 | Tuccillo |
| 2006/0235316 A1* | 10/2006 | Ungless ............... A61B 5/0006 600/509 |
| 2006/0235489 A1 | 10/2006 | Drew et al. |
| 2006/0238333 A1 | 10/2006 | Welch et al. |
| 2006/0241641 A1 | 10/2006 | Albans et al. |

(56) References Cited

U.S. PATENT DOCUMENTS

| | | |
|---|---|---|
| 2006/0241701 A1 | 10/2006 | Markowitz et al. |
| 2006/0241722 A1 | 10/2006 | Thacker et al. |
| 2006/0247545 A1 | 11/2006 | St. Martin |
| 2006/0252999 A1 | 11/2006 | Devaul et al. |
| 2006/0253005 A1 | 11/2006 | Drinan et al. |
| 2006/0253044 A1 | 11/2006 | Zhang et al. |
| 2006/0258952 A1 | 11/2006 | Stahmann et al. |
| 2006/0264730 A1 | 11/2006 | Stivoric et al. |
| 2006/0264767 A1 | 11/2006 | Shennib |
| 2006/0264776 A1 | 11/2006 | Stahmann et al. |
| 2006/0271116 A1 | 11/2006 | Stahmann et al. |
| 2006/0276714 A1 | 12/2006 | Holt et al. |
| 2006/0281981 A1 | 12/2006 | Jang et al. |
| 2006/0281996 A1 | 12/2006 | Kuo et al. |
| 2006/0293571 A1 | 12/2006 | Bao et al. |
| 2006/0293609 A1 | 12/2006 | Stahmann et al. |
| 2007/0010721 A1 | 1/2007 | Chen et al. |
| 2007/0010750 A1 | 1/2007 | Ueno et al. |
| 2007/0015973 A1 | 1/2007 | Nanikashvili |
| 2007/0015976 A1 | 1/2007 | Miesel et al. |
| 2007/0016089 A1 | 1/2007 | Fischell et al. |
| 2007/0021678 A1 | 1/2007 | Beck et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027388 A1 | 2/2007 | Chou |
| 2007/0027497 A1 | 2/2007 | Parnis |
| 2007/0032749 A1 | 2/2007 | Overall et al. |
| 2007/0038038 A1 | 2/2007 | Stivoric et al. |
| 2007/0038078 A1 | 2/2007 | Osadchy |
| 2007/0038255 A1 | 2/2007 | Kieval et al. |
| 2007/0038262 A1 | 2/2007 | Kieval et al. |
| 2007/0043301 A1 | 2/2007 | Martinsen et al. |
| 2007/0043303 A1 | 2/2007 | Osypka et al. |
| 2007/0048224 A1 | 3/2007 | Howell et al. |
| 2007/0060800 A1 | 3/2007 | Drinan et al. |
| 2007/0060802 A1 | 3/2007 | Ghevondian et al. |
| 2007/0069887 A1 | 3/2007 | Welch et al. |
| 2007/0073132 A1 | 3/2007 | Vosch |
| 2007/0073168 A1 | 3/2007 | Zhang et al. |
| 2007/0073181 A1 | 3/2007 | Pu et al. |
| 2007/0073361 A1 | 3/2007 | Goren et al. |
| 2007/0082189 A1 | 4/2007 | Gillette |
| 2007/0083092 A1 | 4/2007 | Rippo et al. |
| 2007/0092862 A1 | 4/2007 | Gerber |
| 2007/0100666 A1 | 5/2007 | Stivoric et al. |
| 2007/0104840 A1 | 5/2007 | Singer |
| 2007/0106132 A1 | 5/2007 | Elhag et al. |
| 2007/0106137 A1 | 5/2007 | Baker, Jr. et al. |
| 2007/0106167 A1 | 5/2007 | Kinast |
| 2007/0118039 A1 | 5/2007 | Bodecker et al. |
| 2007/0123756 A1 | 5/2007 | Kitajima et al. |
| 2007/0123903 A1 | 5/2007 | Raymond et al. |
| 2007/0123904 A1 | 5/2007 | Stad et al. |
| 2007/0129622 A1 | 6/2007 | Bourget et al. |
| 2007/0129643 A1 | 6/2007 | Kwok et al. |
| 2007/0129769 A1 | 6/2007 | Bourget et al. |
| 2007/0142715 A1 | 6/2007 | Banet et al. |
| 2007/0142732 A1 | 6/2007 | Brockway et al. |
| 2007/0149282 A1 | 6/2007 | Lu et al. |
| 2007/0150008 A1 | 6/2007 | Jones et al. |
| 2007/0150009 A1 | 6/2007 | Kveen et al. |
| 2007/0150029 A1 | 6/2007 | Bourget et al. |
| 2007/0162089 A1 | 7/2007 | Mosesov |
| 2007/0167753 A1 | 7/2007 | Van Wyk et al. |
| 2007/0167848 A1 | 7/2007 | Kuo et al. |
| 2007/0167849 A1 | 7/2007 | Zhang et al. |
| 2007/0167850 A1 | 7/2007 | Russell et al. |
| 2007/0172424 A1 | 7/2007 | Roser |
| 2007/0173705 A1 | 7/2007 | Teller et al. |
| 2007/0180047 A1 | 8/2007 | Dong et al. |
| 2007/0180140 A1 | 8/2007 | Welch et al. |
| 2007/0191723 A1 | 8/2007 | Prystowsky et al. |
| 2007/0207858 A1 | 9/2007 | Breving |
| 2007/0208233 A1 | 9/2007 | Kovacs |
| 2007/0208235 A1 | 9/2007 | Besson et al. |
| 2007/0208262 A1 | 9/2007 | Kovacs |
| 2007/0232867 A1 | 10/2007 | Hansmann |
| 2007/0244403 A1 | 10/2007 | Natarajan et al. |
| 2007/0249946 A1 | 10/2007 | Kumar et al. |
| 2007/0250121 A1 | 10/2007 | Miesel et al. |
| 2007/0255120 A1 | 11/2007 | Rosnov |
| 2007/0255153 A1 | 11/2007 | Kumar et al. |
| 2007/0255184 A1 | 11/2007 | Shennib |
| 2007/0255531 A1 | 11/2007 | Drew |
| 2007/0260133 A1 | 11/2007 | Meyer |
| 2007/0260155 A1 | 11/2007 | Rapoport et al. |
| 2007/0260289 A1 | 11/2007 | Giftakis et al. |
| 2007/0270678 A1 | 11/2007 | Fadem et al. |
| 2007/0273504 A1 | 11/2007 | Tran |
| 2007/0276273 A1 | 11/2007 | Watson, Jr. |
| 2007/0282173 A1 | 12/2007 | Wang et al. |
| 2007/0299325 A1 | 12/2007 | Farrell et al. |
| 2008/0004499 A1 | 1/2008 | Davis |
| 2008/0004547 A1 | 1/2008 | Dinsmoor et al. |
| 2008/0004904 A1 | 1/2008 | Tran |
| 2008/0021336 A1 | 1/2008 | Dobak |
| 2008/0024293 A1 | 1/2008 | Stylos |
| 2008/0024294 A1 | 1/2008 | Mazar |
| 2008/0033260 A1 | 2/2008 | Sheppard et al. |
| 2008/0039700 A1 | 2/2008 | Drinan et al. |
| 2008/0058614 A1 | 3/2008 | Banet et al. |
| 2008/0058656 A1 | 3/2008 | Costello et al. |
| 2008/0059239 A1 | 3/2008 | Gerst et al. |
| 2008/0091089 A1 | 4/2008 | Guillory et al. |
| 2008/0114220 A1 | 5/2008 | Banet et al. |
| 2008/0120784 A1 | 5/2008 | Warner et al. |
| 2008/0139934 A1 | 6/2008 | McMorrow et al. |
| 2008/0146892 A1 | 6/2008 | LeBoeuf et al. |
| 2008/0167538 A1 | 7/2008 | Teller et al. |
| 2008/0171918 A1 | 7/2008 | Teller et al. |
| 2008/0171922 A1 | 7/2008 | Teller et al. |
| 2008/0171929 A1 | 7/2008 | Katims |
| 2008/0183052 A1 | 7/2008 | Teller et al. |
| 2008/0200774 A1 | 8/2008 | Luo |
| 2008/0214903 A1 | 9/2008 | Orbach |
| 2008/0220865 A1 | 9/2008 | Hsu |
| 2008/0221399 A1 | 9/2008 | Zhou et al. |
| 2008/0221402 A1 | 9/2008 | Despotis |
| 2008/0224852 A1 | 9/2008 | Dicks et al. |
| 2008/0228084 A1 | 9/2008 | Bedard et al. |
| 2008/0275465 A1 | 11/2008 | Paul et al. |
| 2008/0287751 A1 | 11/2008 | Stivoric et al. |
| 2008/0287752 A1 | 11/2008 | Stroetz et al. |
| 2008/0293491 A1 | 11/2008 | Wu et al. |
| 2008/0294019 A1 | 11/2008 | Tran |
| 2008/0294020 A1 | 11/2008 | Sapounas |
| 2008/0318681 A1 | 12/2008 | Rofougaran et al. |
| 2008/0319279 A1 | 12/2008 | Ramsay et al. |
| 2008/0319282 A1 | 12/2008 | Tran |
| 2008/0319290 A1 | 12/2008 | Mao et al. |
| 2009/0005016 A1 | 1/2009 | Eng et al. |
| 2009/0018410 A1 | 1/2009 | Coene et al. |
| 2009/0018456 A1 | 1/2009 | Hung |
| 2009/0048526 A1 | 2/2009 | Aarts |
| 2009/0054737 A1 | 2/2009 | Magar et al. |
| 2009/0062670 A1 | 3/2009 | Sterling et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |

(56) References Cited

U.S. PATENT DOCUMENTS

| | | | |
|---|---|---|---|
| 2009/0076397 A1 | 3/2009 | Libbus et al. | |
| 2009/0076401 A1 | 3/2009 | Mazar et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0177145 A1 | 7/2009 | Ohlander et al. | |
| 2009/0182204 A1 | 7/2009 | Semler et al. | |
| 2009/0234410 A1 | 9/2009 | Libbus et al. | |
| 2009/0264792 A1 | 10/2009 | Mazar | |
| 2009/0292194 A1 | 11/2009 | Libbus et al. | |
| 2010/0056881 A1 | 3/2010 | Libbus et al. | |
| 2010/0069735 A1* | 3/2010 | Berkner | A61B 5/04028 600/382 |
| 2010/0191310 A1 | 7/2010 | Bly et al. | |
| 2015/0087921 A1* | 3/2015 | Felix | A61B 5/04087 600/301 |
| 2015/0087922 A1* | 3/2015 | Bardy | A61B 5/02055 600/301 |
| 2015/0087923 A1* | 3/2015 | Bardy | A61B 5/04087 600/301 |
| 2015/0087949 A1* | 3/2015 | Felix | A61B 5/04087 600/382 |
| 2015/0087950 A1* | 3/2015 | Felix | A61B 5/04087 600/382 |
| 2015/0094557 A1* | 4/2015 | Hsu | A61B 5/6833 600/391 |
| 2016/0007872 A1* | 1/2016 | Bishay | A61B 5/0452 600/382 |
| 2016/0007875 A1* | 1/2016 | Felix | A61B 5/04087 600/382 |
| 2016/0007877 A1* | 1/2016 | Felix | A61B 5/04325 600/523 |
| 2016/0150989 A1* | 6/2016 | Felix | A61B 5/04017 600/523 |

FOREIGN PATENT DOCUMENTS

| | | |
|---|---|---|
| EP | 1579801 A1 | 9/2005 |
| GB | 2 425 181 A | 10/2006 |
| JP | 2005-521448 | 7/2005 |
| WO | WO 95/07048 | 3/1995 |
| WO | WO 00/79255 | 12/2000 |
| WO | 01/89362 A2 | 11/2001 |
| WO | WO 02/092101 | 11/2002 |
| WO | WO 03/082080 | 10/2003 |
| WO | WO 2005/051164 | 6/2005 |
| WO | WO 2005/104930 | 11/2005 |
| WO | WO 2006/008745 | 1/2006 |
| WO | WO 2006/102476 | 9/2006 |
| WO | WO 2006/111878 A1 | 11/2006 |
| WO | WO 2007/041783 | 4/2007 |
| WO | WO 2007/038607 A2 | 5/2007 |
| WO | WO 2007/094729 A1 | 8/2007 |
| WO | 2007/106455 A2 | 9/2007 |
| WO | 2009/116906 A1 | 9/2009 |

OTHER PUBLICATIONS

Pinna et al., "Home telemonitoring of respiratory activity and heart rate variability in chronic heart failure patients: the challenge of the home or hospital in heart failure project," Computers in Cardiology (2003) 30: 197-200.
"Acute Decompensated Heart Failure"—Wikipedia Entry, downloaded from: <http://en.wikipedia.org/wiki/Acute_decompensated_heart_failure>, submitted version downloaded Feb. 11, 2011, 6 pages total.
"Heart Failure"—Wikipedia Entry, downloaded from the Internet: <http://en.wikipedia.org/wiki/Heart_failure>, submitted version downloaded Feb. 11, 2011, 17 pages total.
3M Corporation, "3M Surgical Tapes—Choose the Correct Tape" quicksheet (2004).
Cooley, "The Parameters of Transthoracic Electical Conduction," Annals of the New York Academy of Sciences, 1970; 170(2):702-713.
EM Microelectronic—Marin SA, "Plastic Flexible LCD," [product brochure]; retrieved from the Internet: <<http://www.em-microelectronic.com/Line.asp?IdLine=48>>, copyright 2009, 2 pages total.
HRV Enterprises, LLC, "Heart Rate Variability Seminars," downloaded from the Internet: <<http://hrventerprise.com/>> on Apr. 24, 2008, 3 pages total.
HRV Enterprises, LLC, "LoggerPro HRV Biosignal Analysis," downloaded from the Internet: <<http://hrventerprise.com/products.html>> on Apr. 24, 2008, 3 pages total.
International Search Report and Written Opinion of PCT Application No. PCT/US08/76217, dated Nov. 10, 2008, 16 pages total.
AD5934: 250 kSPS 12-Bit Impedance Converter Network Analyzer, Analog Devices, retrieved from the Internet: <<http://www.analog.com/static/imported-files/data_sheets/AD5934.pdf>>, 40 pages.
Something in the way he moves, The Economist, 2007, retrieved from the Internet: <<http://www.economist.com/science/printerFriendly.cfm?story id=9861412>>.
Abraham, "New approaches to monitoring heart failure before symptoms appear," Rev Cardiovasc Med. 2006 ;7 Suppl 1 :33-41.
Adams, Jr. "Guiding heart failure care by invasive hemodynamic measurements: possible or useful?", Journal of Cardiac Failure 2002; 8(2):71-73.
Adamson et al., "Continuous autonomic assessment in patients with symptomatic heart failure: prognostic value of heart rate variability measured by an implanted cardiac resynchronization device ," Circulation. 2004;110:2389-2394.
Adamson et al., "Ongoing right ventricular hemodynamics in heart failure," J Am Coll Cardiol, 2003; 41:565-57.
Adamson, "Integrating device monitoring into the infrastructure and workflow of routine practice," Rev Cardiovasc Med. 2006 ;7 Suppl 1:42-6.
Adhere [presentation], "Insights from thedhere Registry: Data from over 100,000 patient cases," 70 pages total.
Advamed White Sheet, "Health Information Technology: Improving Patient Safety and Quality of Care," Jun. 2005, 23 pages.
Aghababian, "Acutely decompensated heart failure: opportunities to improve care and outcomes in the emergency department," Rev Cardiovasc Med. 2002;3 Suppl 4:S3-9.
Albert, "Bioimpedance to prevent heart failure hospitalization," Curr Heart Fail Rep. Sep. 2006;3(3):136-42.
American Heart Association, "Heart Disease and Stroke Statistics—2006 Update," 2006, 43 pages.
American Heart Association, "Heart Disease and Stroke Statistics—2007 Update. A Report from the American Heart Association Statistics Committee and Stroke Statistics Subcommittee," Circulation 2007; 115;e69-e171.
Belalcazar et al., "Monitoring lung edema using the pacemaker pulse and skin electrodes," Physiol. Meas. 2005; 26:S153-S163.
Bennet, "Development of implantable devices for continuous ambulatory monitoring of central hemodynamic values in heart failure patients," PACE Jun. 2005; 28:573-584.
Bourge, "Case studies in advanced monitoring with the chronicle device," Rev Cardiovasc Med. 2006 ;7 Suppl 1:S56-61.
Braunschweig, "Continous haemodynamic monitoring during withdrawal of diuretics in patients with congestive heart failure," European Heart Journal 2002 23(1):59-69.
Braunschweig, "Dynamic changes in right ventricular pressures during haemodialysis recorded with an implantable haemodynamic monitor ," Nephrol Dial Transplant 2006; 21:176-183.
Brennan, "Measuring a Grounded Impedance Profile Using the AD5933," Analog Devices, retrieved from the internet <<http://http://www.analog.com/static/imported-files/application_notes/427095282381510189AN847_0.pdf>>, 12 pages total.
Buono et al., "The effect of ambient air temperature on whole-body bioelectrical impedance," Physiol. Meas. 2004;25:119-123.
Burkhoff et al., "Heart failure with a normal ejection fraction: Is it really a disorder of diastolic function?" Circulation 2003; 107:656-658.

(56) References Cited

OTHER PUBLICATIONS

Burr et al., "Heart rate variability and 24-hour minimum heart rate," Biological Research for Nursing, 2006; 7(4):256-267.
Cardionet, "CardioNet Mobile Cardiac Outpatient Telemetry: Addendum to Patient Education Guide", CardioNet, Inc., 2007, 2 pages.
Cardionet, "Patient Education Guide", CardioNet, Inc., 2007, 7 pages. Undated.
Charach et al., "Transthoracic monitoring of the impedance of the right lung in patients with cardiogenic pulmonary edema," Crit Care Med Jun. 2001;29(6):1137-1144.
Charlson et al., "Can disease management target patients most likely to generate high costs? The Impact of Comorbidity," Journal of General Internal Medicine, Apr. 2007, 22(4):464-469.
Chaudhry et al., "Telemonitoring for patients with chronic heart failure: a systematic review," J Card Fail. Feb. 2007; 13(1): 56-62.
Chung et al., "White coat hypertension: Not so benign after all?," Journal of Human Hypertension (2003) 17, 807-809.
Cleland et al., "The EuroHeart Failure survey programme—a survey on the quality of care among patients with heart failure in Europe—Part 1: patient characteristics and diagnosis," European Heart Journal 2003 24(5):442-463.
Cowie et al., "Hospitalization of patients with heart failure. A population-based study," European Heart Journal 2002 23(11):877-885.
Dimri, Chapter 1: Fractals in geophysics and seimology: an introduction, *Fractal Behaviour of the Earth System,* Springer Berlin Heidelberg 2005, pp. 1-22. [Summary and 1st page Only].
El-Dawlatly et al., "Impedance cardiography: noninvasive assessment of hemodynamics and thoracic fluid content during bariatric surgery," Obesity Surgery, May 2005, 15(5):655-658.
Erdmann, "Editorials: The value of diuretics in chronic heart failure demonstrated by an implanted haemodynamic monitor," European Heart Journal 2002 23(1):7-9.
FDA—Medtronic Inc., Chronicle 9520B Implantable Hemodynamic Monitor Reference Manual, 2007, 112 pages.
FDA Executive Summary Memorandum, prepared for Mar. 1, 2007, meeting of the Circulatory Systems Devices Advisory Panel, P050032 Medtronic, Inc. Chronicle Implantable Hemodynamic Monitor (IHM) System, 23 pages. Retrieved from the Internet: <<http://www.fda.gov/ohrms/dockets/ac/07/briefing/2007-4284b1_02.pdf>>.
FDA Executive Summary, Medtronic Chronicle Implantable Hemodynamic Monitoring System P050032: Panel Package Sponsor Executive Summary; vol. 1, section 4: Executive Summary. 12 pages total. Retrieved from the Internet: <<http://www.fda.gov/OHRMS/DOCKETS/AC/07/briefing/2007-4284b1_03.pdf>>.
FDA—Medtronic Chronicle Implantable Hemodynamic Monitoring System P050032: Panel Package Section 11: Chronicle IHM Summary of Safety and Effectiveness, 2007; retrieved from the Internet: <http://www.fda.gov/OHRMS/DOCKETS/AC/07/briefing/2007-4284b1_04.pdf>, 77 pages total.
FDA, Draft questions for Chronicle Advisory Panel Meeting, 3 pages. Retrieved from the Internet: <<http://www.fda/gov/ohrms/dockets/ac/07/questions/2007-4284q1_draft.pdf>>.
FDA, References for Mar. 1 Circulatory System Devices Panel, 1 page total. 2007. Retrieved from the Internet: <<http://www.fda.gov/OHRMS/DOCKETS/AC/07/briefing/2007-4284bib1_01.pdf>>.
FDA Panel Recommendation, "Chronicle Analysis," Mar. 1, 2007, 14 pages total.
Fonarow et al., "Risk stratification for in-hospital mortality in acutely decompensated heart failure: classification and regression tree analysis," JAMA. Feb. 2, 2005;293(5):572-580.
Fonarow, "How well are chronic heart failure patients being managed?", Rev Cardiovasc Med. 2006;7 Suppl 1:S3-11.
Fonarow, "Maximizing Heart Failure Care" [Powerpoint Presentation], downloaded from the Internet <<http://www.medreviews.com/media/MaxHFCore.ppt>>, 130 pages total.
Fonarow, "Proactive monitoring and management of the chronic heart failure patient," Rev Cardiovasc Med. 2006; 7 Suppl 1:S1-2.
Fonarow, "The Acute Decompensated Heart Failure National Registry (ADHERE): opportunities to improve care of patients hospitalized with acute decompensated heart failure," Rev Cardiovasc Med. 2003;4 Suppl 7:S21-S30.
Ganion et al., "Intrathoracic impedance to monitor heart failure status: a comparison of two methods in a chronic heart failure dog model," Congest Heart Fail. Jul.-Aug. 2005;11(4):177-81, 211.
Gass et al., "Critical pathways in the management of acute decompensated heart failure: A CME-Accredited monograph," Mount Sinai School of Medicine, 2004, 32 pages total.
Gheorghiade et al., "Congestion is an important diagnostic and therapeutic target in heart failure," Rev Cardiovasc Med. 2006 ;7 Suppl 1 :12-24.
Gilliam, III et al., "Changes in heart rate variability, quality of life, and activity in cardiac resynchronization therapy patients: results of the HF-HRV registry," Pacing and Clinical Electrophysiology, Jan. 18, 2007; 30(1): 56-64.
Gilliam, III et al., "Prognostic value of heart rate variability footprint and standard deviation of average 5-minute intrinsic R-R intervals for mortality in cardiac resynchronization therapy patients.," J Electrocardiol. Oct. 2007;40(4):336-42.
Gniadecka, "Localization of dermal edema in lipodermatosclerosis, lymphedema, and cardiac insufficiency high-frequency ultrasound examination of intradermal echogenicity," J Am Acad oDermatol, Jul. 1996; 35(1):37-41.
Goldberg et al., "Randomized trial of a daily electronic home monitoring system in patients with advanced heart failure: The Weight Monitoring in Heart Failure (WHARF) Trial," American Heart Journal, Oct. 2003; 416(4):705-712.
Grap et al., "Actigraphy in the Critically Ill: Correlation With Activity, Agitation, and Sedation," American Journal of Critical Care. 2005;14: 52-60.
Gudivaka et al., "Single- and multifrequency models for bioelectrical impedance analysis of body water compartments," J Appl Physiol, 1999;87(3):1087-1096.
Guyton et al., Unit V: The Body Fluids and Kidneys, Chapter 25: The Body Fluid Compartments: Extracellular and Intracellular Fluids; Interstitial Fluid and Edema, *Guyton & Hall Textbook of Medical Physiology* 11th Edition, Saunders 2005; pp. 291-306.
Hadase et al., "Very low frequency power of heart rate variability is a powerful predictor of clinical prognosis in patients with congestive heart Failure," Circ J 2004; 68(4):343-347.
Hallstrom et al., "Structural relationships between measures based on heart beat intervals: potential for improved risk assessment," IEEE Biomedical Engineering 2004, 51(8):1414-1420.
HFSA 2006 Comprehensive Heart Failure Practice Guideline— Executive Summary: HFSA 2006 Comprehensive Heart Failure Practice Guideline, Journal of Cardiac Failure 2006;12(1):10-e38.
HFSA 2006 Comprehensive Heart Failure Practice Guideline— Section 12: Evaluation and Management of Patients With Acute Decompensated Heart Failure, Journal of Cardiac Failure 2006;12(1):e86-e103.
HFSA 2006 Comprehensive Heart Failure Practive Guideline— Section 2: Conceptualization and Working Definition of Heart Failure, Journal of Cardiac Failure 2006;12(1):e10-e11.
HFSA 2006 Comprehensive Heart Failure Practice Guideline— Section 3: Prevention of Ventricular Remodeling Cardiac Dysfunction, and Heart Failure Overview, Journal of Cardiac Failure 2006;12(1):e12-e15.
HFSA 2006 Comprehensive Heart Failure Practice Guideline— Section 4: Evaluation of Patients for Ventricular Dysfunction and Heart Failure, Journal of Cardiac Failure 2006;12(1):e16-e25.
HFSA 2006 Comprehensive Heart Failure Practice Guideline— Section 8: Disease Management in Heart Failure Education and Counseling, Journal of Cardiac Failure 2006;12(1):e58-e68.
Hunt et al., "ACC/AHA 2005 Guideline Update for the Diagnosis and Management of Chronic Heart Failure in the Adult: A Report of the American College of Cardiology/American Heart Association Task Force on Practice Guidelines (Writing Committee to Update the 2001 Guidelines for the Evaluation and Management of Heart Failure): Developed in Collaboration With the American College of

(56) References Cited

OTHER PUBLICATIONS

Chest Physicians and the International Society for Heart and Lung Transplantation: Endorsed by the Heart Rhythm Society," Circulation. 2005;112:e154-e235.

Hunt et al., ACC/AHA Guidelines for the Evaluation and Management of Chronic Heart Failure in the Adult: Executive Summary a Report of the American College of Cardiology/American Heart Association Task Force on Practice Guidelines (Committee to Revise the 1995 Guidelines for the Evaluation and Management of Heart Failure), Circulation. 2001;104:2996-3007.

Imhoff et al., "Noninvasive whole-body electrical bioimpedance cardiac output and invasive thermodilution cardiac output in high-risk surgical patients," Critical Care Medicine 2000; 28(8):2812-2818.

Jaeger et al., "Evidence for Increased Intrathoracic Fluid Volume in Man at High Altitude," J Appl Physiol 1979; 47(6): 670-676.

Jerant et al., "Reducing the cost of frequent hospital admissions for congestive heart failure: a randomized trial of a home telecare intervention," Medical Care 2001, 39(11):1234-1245.

Jaio et al., "Variance fractal dimension analysis of seismic refraction signals," WESCANEX 97: Communications, Power and Computing. IEEE Conference Proceedings., May 22-23, 1997, pp. 163-167 [Abstract Only].

Kasper et al., "A randomized trial of the efficacy of multidisciplinary care in heart failure: outpatients at high risk of hospital readmission," J Am Coll Cardiol, 2002; 39:471-480.

Kaukinen, "Cardiac output measurement after coronary artery bypass grafting using bolus thermodilution, continuous thermodilution, and whole-body impedance cardiography," Journal of Cardiothoracic and Vascular Anesthesia 2003; 17(2):199-203.

Kawaguchi et al., "Combined ventricular systolic and arterial stiffening in patients with heart failure and preserved ejection fraction: implications for systolic and diastolic reserve limitations," Circulation. 2003;107:714-720.

Kawasaki et al., "Heart rate turbulence and clinical prognosis in hypertrophic cardiomyopathy and myocardial infarction," Circ J. Jul. 2003;67(7):601-604.

Kearney et al., "Predicting death due to progressive heart failure in patients with mild-to-moderate chronic heart failure," J Am Coll Cardiol, 2002; 40(10):1801-1808.

Kitzman et al., "Pathophysiological characterization of isolated diastolic heart failure in comparison to systolic heart failure," JAMA Nov. 2002; 288(17):2144-2150.

Kööbi et al., "Non-invasive measurement of cardiac output : whole-body impedance cardiography in simultaneous comparison with thermodilution and direct oxygen Fick methods," Intensive Care Medicine 1997; 23(11):1132-1137.

Koyama et al., "Evaluation of heart-rate turbulence as a new prognostic marker in patients with chronic heart failure," Circ J 2002; 66(10):902-907.

Krumholz et al., "Predictors of readmission among elderly survivors of admission with heart failure," American Heart Journal 2000; 139(1):72-77.

Kyle et al., "Bioelectrical Impedance Analysis—part I: review of principles and methods," Clin Nutr. Oct. 2004;23(5):1226-1243.

Kyle et al., "Bioelectrical Impedance Analysis—part II: utilization in clinical practice," Clin Nutr. Oct. 2004;23(5):1430-1453.

Lee et al., "Predicting mortality among patients hospitalized for heart failure: derivation and validation of a clinical model," JAMA 2003;290(19):2581-2587.

Leier "The Physical Examination in Heart Failure—Part I," Congest Heart Fail. Jan.-Feb. 2007;13(1):41-47.

LifeShirt® Model 200 Directions for Use, "Introduction", VivoMetrics, Inc. 9 page total.

Liu et al., "Fractal analysis with applications to seismological pattern recognition of underground nuclear explosions," Singal Processing, Sep. 2000, 80(9):1849-1861. [Abstract Only].

Lozano-Nieto, "Impedance ratio in bioelectrical impedance measurements for body fluid shift determination," Proceedings of the IEEE 24th Annual Northeast Bioengineering. Conference, Apr. 9-10, 1998, pp. 24-25.

Lucreziotti et al., "Five-minute recording of heart rate variability in severe chronic heart failure : Correlates with right ventricular function and prognostic implications," American Heart Journal 2000; 139(6):1088-1095.

Lüthje et al., "Detection of heart failure decompensation using intrathoracic impedance monitoring by a triple-chamber implantable defibrillator," Heart Rhythm Sep. 2005;2(9):997-999.

Magalski et al., "Continuous ambulatory right heart pressure measurements with an implantable hemodynamic monitor: a multicenter, 12-Month Follow-up Study of Patients With Chronic Heart Failure," J Card Fail 2002, 8(2):63-70.

Mahlberg et al., "Actigraphy in agitated patients with dementia: Monitoring treatment outcomes," Zeitschrift für Gerontologie und Geriatrie, Jun. 2007; 40(3)178-184. [Abstract Only].

Matthie et al., "Analytic assessment of the various bioimpedance methods used to estimate body water," Appl Physiol 1998; 84(5):1801-1816.

Matthie, "Second generation mixture theory equation for estimating intracellular water using bioimpedance spectroscopy," J Appl Physiol 2005; 99:780-781.

McMurray et al., "Heart Failure: Epidemiology, Aetiology, and Prognosis of Heart Failure," Heart 2000;83:596-602.

Miller, "Home monitoring for congestive heart failure patients," Caring Magazine, Aug. 1995: 53-54.

Moser et al., "Improving outcomes in heart failure: it's not unusual beyond usual Care," Circulation. 2002;105:2810-2812.

Nagels et al., "Actigraphic measurement of agitated behaviour in dementia," International journal of geriatric psychiatry , 2009; 21(4):388-393. [Abstract Only].

Nakamura et al., "Universal scaling law in human behavioral organization," Physical Review Letters, Sep. 28, 2007; 99(13):138103 (4 pages).

Nakaya, "Fractal properties of seismicity in regions affected by large, shallow earthquakes in western Japan: Implications for fault formation processes based on a binary fractal fracture network model," Journal of geophysical research, Jan. 2005; 11(B1):B01310.1-B01310.15. [Abstract Only].

Naylor et al., "Comprehensive discharge planning for the hospitalized elderly: a randomized clinical trial ," Amer. College Physicians 1994; 120(12):999-1006.

Nesiritide (Natrecor),, [Presentation] Acutely Decompensated Congestive Heart Failure: Burden of Disease, downloaded from the Internet: <<http://www.huntsvillehospital.org/foundation/events/cardiologyupdate/CHF.ppt.>>, 39 pages.

Nieminen et al., "EuroHeart Failure Survey II (EHFS II): a survey on hospitalized acute heart failure patients: description of population," European Heart Journal 2006; 27(22):2725-2736.

Nijsen et al., "The potential value of three-dimensional accelerometry for detection of motor seizures in severe epilepsy," Epilepsy Behav. Aug. 2005;7(1):74-84.

Noble et al., "Diuretic induced change in lung water assessed by electrical impedance tomography," Physiol. Meas. 2000; 21(1):155-163.

Noble et al., "Monitoring patients with left ventricular failure by electrical impedance tomography," Eur J Heart Fail. Dec. 1999;1(4):379-84.

O'Connell et al., "Economic impact of heart failure in the United States: time for a different approach," J Heart Lung Transplant., Jul.-Aug. 1994 ; 13(4):S107-S112.

Ohlsson et al., "Central hemodynamic responses during serial exercise tests in heart failure patients using implantable hemodynamic monitors," Eur J Heart Fail. Jun. 2003;5(3):253-259.

Ohlsson et al., "Continuous ambulatory monitoring of absolute right ventricular pressure and mixed venous oxygen saturation in patients with heart failure using an implantable haemodynamic monitor," European Heart Journal 2001 22(11):942-954.

(56) References Cited

OTHER PUBLICATIONS

Packer et al., "Utility of impedance cardiography for the identification of short-term risk of clinical decompensation in stable patients with chronic heart failure," J Am Coll Cardiol, 2006; 47(11):2245-2252.
Palatini et al., "Predictive value of clinic and ambulatory heart rate for mortality in elderly subjects with systolic hypertension" Arch Intern Med. 2002;162:2313-2321.
Piiria et al., "Crackles in patients with fibrosing alveolitis bronchiectasis, COPD, and Heart Failure," Chest May 1991; 99(5):1076-1083.
Pocock et al., "Predictors of mortality in patients with chronic heart failure," Eur Heart J 2006; (27): 65-75.
Poole-Wilson, "Importance of control of fluid volumes in heart failure," European Heart Journal 2000; 22(11):893-894.
Raj et al., 'Letter Regarding Article by Adamson et al, "Continuous Autonomic Assessment in Patients With Symptomatic Heart Failure: Prognostic Value of Heart Rate Variability Measured by an Implanted Cardiac Resynchronization Device"', Circulation 2005;112:e37-e38.
Ramirez et al., "Prognostic value of hemodynamic findings from impedance cardiography in hypertensive stroke," AJH 2005; 18(20):65-72.
Rich et al., "A multidisciplinary intervention to prevent the readmission of elderly patients with congestive heart failure," New Engl. J. Med. 1995;333:1190-1195.
Roglieri et al., "Disease management interventions to improve outcomes in congestive heart failure," Am J Manag Care. Dec. 1997;3(12):1831-1839.
Sahalos et al., "The Electrical impedance of the human thorax as a guide in evaluation of intrathoracic fluid volume," Phys. Med. Biol. 1986; 31:425-439.
Saxon et al., "Remote active monitoring in patients with heart failure (rapid-rf): design and rationale," Journal of Cardiac Failure 2007; 13(4):241-246.
Scharf et al., "Direct digital capture of pulse oximetry waveforms," Proceedings of the Twelfth Southern Biomedical Engineering Conference, 1993., pp. 230-232.
Shabetai, "Monitoring heart failure hemodynamics with an implanted device: its potential to improve outcome," J Am Coll Cardiol, 2003; 41:572-573.
Small, "Integrating monitoring into the Infrastructure and Workflow of Routine Practice: OptiVol," Rev Cardiovasc Med. 2006 ;7 Supp 1: S47-S55.
Smith et al., "Outcomes in heart failure patients with preserved ejection fraction: mortality, readmission, and functional decline ," J Am Coll Cardiol, 2003; 41:1510-1518.
Someren, "Actigraphic monitoring of movement and rest-activity rhythms inaging, Alzheimer's disease, and Parkinson's disease," IEEE Transactions on Rehabilitation Engineering, Dec. 1997; 5(4):394-398. [Abstract Only].
Starling, "Improving care of chronic heart failure: advances from drugs to devices," Cleveland Clinic Journal of Medicine Feb. 2003; 70(2):141-146.
Steijaert et al., "The use of multi-frequency impedance to determine total body water and extracellular water in obese and lean female individuals," International Journal of Obesity Oct. 1997; 21(10):930-934.
Stewart et al., "Effects of a home-based intervention among patients with congestive heart failure discharged from acute hospital care," Arch Intern Med. 1998;158:1067-1072.
Stewart et al., "Effects of a multidisciplinary, home-based intervention on planned readmissions and survival among patients with chronic congestive heart failure: a randomised controlled study," The Lancet Sep. 1999, 354(9184):1077-1083.
Stewart et al., "Home-based intervention in congestive heart failure: long-term implications on readmission and surival," Circulation. 2002;105:2861-2866.
Stewart et al., "Prolonged beneficial effects of a home-based intervention on unplanned readmissions and mortality among patients with congestive heart failure," Arch Intern Med. 1999;159:257-261.
Stewart et al., "Trends in Hospitalization for Heart Failure in Scotland, 1990-1996. An Epidemic that has Reached Its Peak?," European Heart Journal 2001 22(3):209-217.
Swedberg et al., "Guidelines for the diagnosis and treatment of chronic heart failure: executive summary (update 2005): The Task Force for the Diagnosis and Treatment of Chronic Heart Failure of the European Society of Cardiology," Eur Heart J. Jun. 2005; 26(11):1115-1140.
Tang, "Case studies in advanced monitoring: OptiVol," Rev Cardiovasc Med. 2006;7 Suppl 1:S62-S66.
The ESCAPE Investigators and ESCAPE Study Coordinators, "Evaluation Study of Congestive Heart Failure and Pulmonary Artery Catheterization Effectiveness," JAMA 2005;294:1625-1633.
Tosi et al., "Seismic signal detection by fractal dimension analysis," Bulletin of the Seismological Society of America; Aug. 1999; 89(4):970-977. [Abstract Only].
Van De Water et al., "Monitoring the chest with impedance," Chest. 1973;64:597-603.
Vasan et al., "Congestive heart failure in subjects with normal versus reduced left ventricular ejection fraction," J Am Coll Cardiol, 1999; 33:1948-1955.
Verdecchia et al., "Adverse prognostic value of a blunted circadian rhythm of heart rate in essential hypertension," Journal of Hypertension 1998; 16(9):1335-1343.
Verdecchia et al., "Ambulatory pulse pressure: a potent predictor of total cardiovascular risk in hypertension," Hypertension. 1998;32:983-988.
Vollmann et al., "Clinical utility of intrathoracic impedance monitoring to alert patients with an implanted device of deteriorating chronic heart failure," Euorpean Heart Journal Advance Access published on Feb. 19, 2007, downloaded from the Internet:<<http://eurheartj.oxfordjournals.org/cgi/content/full/ehl506v1>>, 6 pages total.
Vuksanovic et al., "Effect of posture on heart rate variability spectral measures in children and young adults with heart disease," International Journal of Cardiology 2005;101(2): 273-278.
Wang et al., "Feasibility of using an implantable system to measure thoracic congestion in an ambulatory chronic heart failure canine model," PACE 2005;28(5):404-411.
Wickemeyer et al., #197—"Association between atrial and ventricular tachyarrhythmias, intrathoracic impedance and heart failure decompensation in CRT-D Patients," Journal of Cardiac Failure 2007; 13 (6) Suppl.; S131-132.
Williams et al, "How do different indicators of cardiac pump function impact upon the long-term prognosis of patients with chronic heart failure," American Heart Journal, 150(5):983.e1-983.e6.
Wonisch et al., "Continuous haemodynamic monitoring during exercise in patients with pulmonary hypertension," Int J Cardiol. Jun. 8, 2005;101(3):415-420.
Wynne et al., "Impedance cardiography: a potential monitor for hemodialysis," Journal of Surgical Research 2006, 133(1):55-60.
Yancy "Current approaches to monitoring and management of heart failure," Rev Cardiovasc Med 2006; 7 Suppl 1:S25-32.
Ypenburg et al., "Intrathoracic Impedance Monitoring to Predict Decompensated Heart Failure," Am J Cardiol 2007, 99(4):554-557.
Yu et al., "Intrathoracic Impedance Monitoring in Patients With Heart Failure: Correlation With Fluid Status and Feasibility of Early Warning Preceding Hospitalization," Circulation. 2005;112:841-848.
Zannad et al., "Incidence, clinical and etiologic features, and outcomes of advanced chronic heart failure: The EPICAL Study," J Am Coll Cardiol, 1999; 33(3):734-742.
Zile, "Heart failure with preserved ejection fraction: is this diastolic heart failure?" J Am Coll Cardiol, 2003; 41(9):1519-1522.
U.S. Appl. No. 60/006,600, filed Nov. 13, 1995; inventor: Terry E. Flach.
U.S. Appl. No. 60/972,316, filed Sep. 12, 2008; inventor: Imad Libbus et al.

(56) References Cited

OTHER PUBLICATIONS

U.S. Appl. No. 60/972,329, filed Sep. 14, 2007; inventor: Yatheendhar Manicka et al.
U.S. Appl. No. 60/972,333, filed Sep. 14, 2007; inventor: Mark Bly et al.
U.S. Appl. No. 60/972,336, filed Sep. 14, 2007; inventor: James Kristofer et al.
U.S. Appl. No. 60/972,340, filed Sep. 14, 2007; inventor: James Kristofer et al.
U.S. Appl. No. 60/972,343, filed Sep. 14, 2007; inventor: James Kristofer et al.
U.S. Appl. No. 60/972,354, filed Sep. 14, 2007; inventor: Scott Thomas Mazar et al.
U.S. Appl. No. 60/972,359, filed Sep. 14, 2007; inventor: Badri Amurthur et al.
U.S. Appl. No. 60/972,363, filed Sep. 14, 2007; inventor: Badri Amurthur et al.
U.S. Appl. No. 60/972,512, filed Sep. 14, 2007; inventor: Imad Libbus et al.
U.S. Appl. No. 60/972,537, filed Sep. 14, 2007; inventor: Yatheendhar Manicka et al.
U.S. Appl. No. 60/972,581, filed Sep. 14, 2007; inventor: Imad Libbus et al.
U.S. Appl. No. 60/972,616, filed Sep. 14, 2007; inventor: Imad Libbus et al.
U.S. Appl. No. 60/972,629, filed Sep. 14, 2007; inventor: Mark Bly et al.
U.S. Appl. No. 61/035,970, filed Mar. 12, 2008; inventor: Imad Libbus et al.
U.S. Appl. No. 61/046,196, filed Apr. 18, 2008; inventor: Scott T. Mazar.
U.S. Appl. No. 61/047,875, filed Apr. 25, 2008; inventor: Imad Libbus et al.
U.S. Appl. No. 61/055,645, filed May 23, 2008; inventor: Mark Bly et al.
U.S. Appl. No. 61/055,656, filed May 23, 2008; inventor: Imad Libbus et al.
U.S. Appl. No. 61/055,662, filed May 23, 2008; inventor: Imad Libbus et al.
U.S. Appl. No. 61/055,666, filed May 23, 2008; inventor: Yatheendhar Manicka et al.
U.S. Appl. No. 61/079,746, filed Jul. 10, 2008; inventor: Brett Landrum.
U.S. Appl. No. 61/084,567, filed Jul. 29, 2008; inventor: Mark Bly.

* cited by examiner

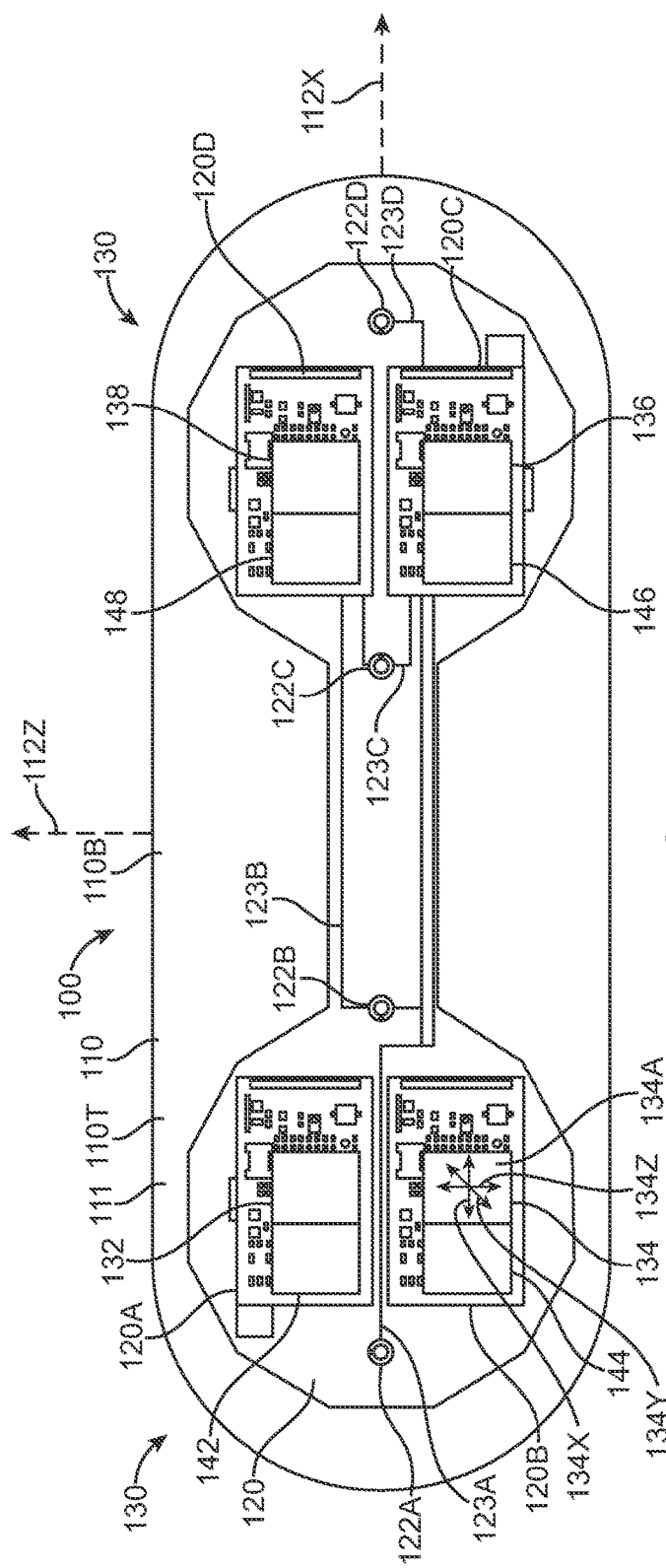
FIG. 1D
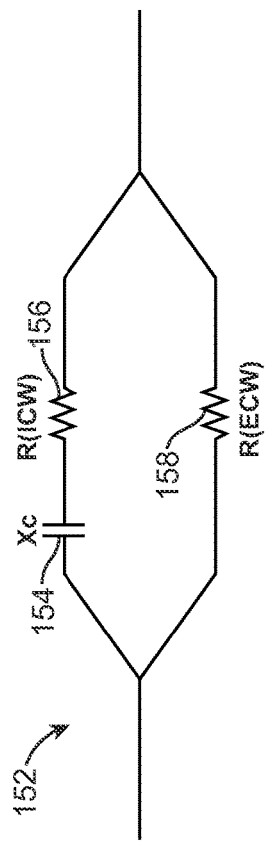
FIG. 1D1

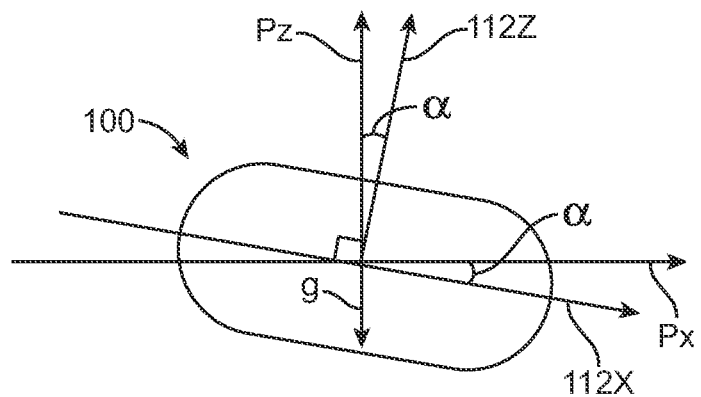
FIG. 1D2
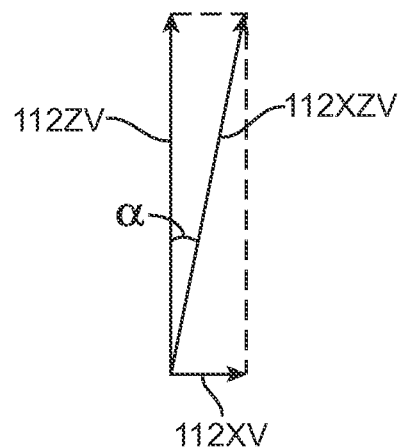
FIG. 1D3

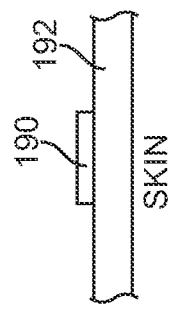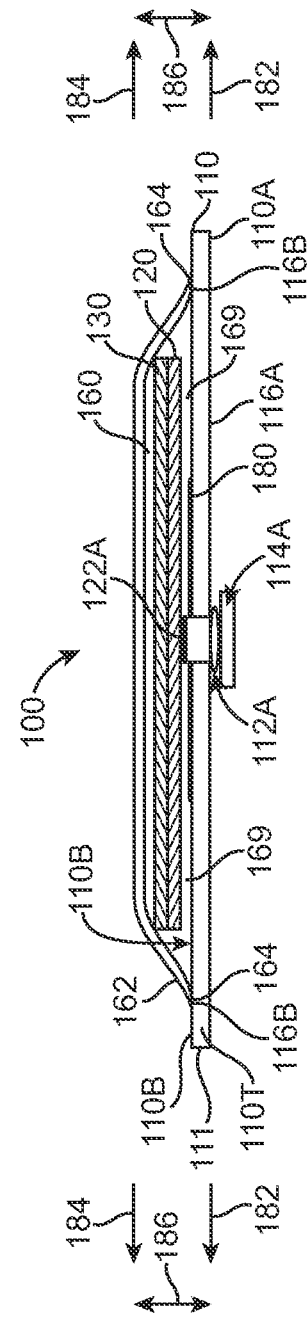

ADHERENT CARDIAC MONITOR WITH ADVANCED SENSING CAPABILITIES

CROSS-REFERENCES TO RELATED APPLICATIONS

The present application is a divisional of U.S. Non-Provisional application Ser. No. 12/209,265 filed on Sep. 12, 2008, which claims the benefit under 35 USC 119(e) of U.S. Provisional Application Nos. 60/972,537 filed Sep. 14, 2007, 61/055,666 and 61/055,662 both of which were filed May 23, 2008; the full disclosures of each of which are incorporated herein by reference in their entirety.

The subject matter of the present application is related to the following applications: 60/972,512; 60/972,329; 60/972,354; 60/972,616; 60/972,363; 60/972,343; 60/972,581; 60/972,629; 60/972,316; 60/972,333; 60/972,359; 60/972,336; 60/972,340 all of which were filed on Sep. 14, 2007; 61/046,196 filed Apr. 18, 2008; 61/047,875 filed Apr. 25, 2008; 61/055,645, 61/055,656 all filed May 23, 2008; and 61/079,746 filed Jul. 10, 2008.

The following applications are being filed concurrently with the present application, on Sep. 12, 2008: U.S. Application No. 12/209,279 entitled "Multi-Sensor Patient Monitor to Detect Impending Cardiac Decompensation Prediction"; 026843-000220US entitled "Adherent Device with Multiple Physiological Sensors"; 026843-000410US entitled "Injectable Device for Physiological Monitoring"; 026843-000510US entitled "Delivery System for Injectable Physiological Monitoring System"; 026843-000620US entitled "Adherent Device for Cardiac Rhythm Management"; 026843-000710US entitled "Adherent Device for Respiratory Monitoring"; 026843-000810US entitled "Adherent Athletic Monitor"; 026843-000910US entitled "Adherent Emergency Monitor"; 026843-001320US entitled "Adherent Device with Physiological Sensors"; 026843-001410US entitled "Medical Device Automatic Start-up upon Contact to Patient Tissue"; 026843-001900US entitled "System and Methods for Wireless Body Fluid Monitoring"; 026843-002410US entitled "Adherent Device for Sleep Disordered Breathing"; 026843-002710US entitled "Dynamic Pairing of Patients to Data Collection Gateways"; 026843-003010US entitled "Adherent Multi-Sensor Device with Implantable Device Communications Capabilities"; 026843-003110US entitled "Data Collection in a Multi-Sensor Patient Monitor"; 026843-003210US entitled "Adherent Multi-Sensor Device with Empathic Monitoring"; 026843-003310US entitled "Energy Management for Adherent Patient Monitor"; and 026843-003410US entitled "Tracking and Security for Adherent Patient Monitor."

BACKGROUND OF THE INVENTION

1. Field of the Invention

The present invention relates to patient monitoring. Although embodiments make specific reference to monitoring impedance and electrocardiogram signals with an adherent patch, the system methods and device described herein may be applicable to many applications in which physiological monitoring is used, for example wireless physiological monitoring for extended periods.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital. One example of a device to provide long term monitoring of a patient is the Holter monitor, or ambulatory electrocardiography device.

In addition to measuring heart signals with electrocardiograms, known physiologic measurements include impedance measurements. For example, transthoracic impedance measurements can be used to measure hydration and respiration.

Work in relation to embodiments of the present invention suggests that known methods and apparatus for long term monitoring of patients may be less than ideal. Although transthoracic measurements can be useful, such measurements may use electrodes that may be somewhat uncomfortable and/or cumbersome for the patient to wear. Also, it would be helpful to detect subtle changes in patient physiology, for example based on subtle changes in electrocardiogram signals and/or patient hydration signals. In at least some instances, electrodes that are held against the skin of the patient can become detached and/or dehydrated, such that the electrodes must be replaced. Replacement of electrodes can result in a change in the orientation of the electrodes that may affect the measured signal in at least some instances. Examples of physiological measurements that may be affected by electrode placement include electrocardiogram signals and tissue impedance signals to measure hydration and/or respiration of a patient. Therefore, a need exists to improve the quality of long term patient measurements with external devices, for example those worn by the patient.

Although implantable devices may be used in some instances, many of these devices can be invasive and/or costly, and may suffer at least some of the shortcomings of known wearable devices.

Therefore, a need exists for improved patient monitoring. Ideally, such improved patient monitoring would avoid at least some of the short-comings of the present methods and devices.

2. Description of the Background Art

The following US Patents and Publications may describe relevant background art: U.S. Pat. Nos. 4,121,573; 4,478,223; 4,850,370; 4,955,381; 4,981,139; 5,080,099; 5,125,412; 5,331,966; 5,353,793; 5,511,553; 5,544,661; 5,558,638; 5,724,025; 5,772,586; 5,862,802; 5,970,986; 5,987,352; 6,047,203; 6,052,615; 6,117,077; 6,129,744; 6,225,901; 6,385,473; 6,416,471; 6,454,707; 6,480,733; 6,496,715; 6,527,711; 6,527,729; 6,551,252; 6,595,927; 6,595,929; 6,605,038; 6,611,705; 6,645,153; 6,699,200; 6,821,249; 6,912,414; 6,881,191; 6,980,851; 7,020,508; 7,054,679; 7,153,262; 7,206,630; 2002/0045836; 2003/0092975; 2003/0149349; 2005/0065445; 2005/0113703; 2005/0131288; 2005/0267381; 2006/0010090; 2006/0031102; 2006/0089679; 2006/0116592; 2006/0122474; 2006/0155183; 2006/0253044; 2006/0224051; 2006/0264730; 2007/0016089; 2007/0021678; 2007/0038038; 2007/0073132; 2007/0142715; 2007/0167849; 2007/0167850; and 2007/0208233.

BRIEF SUMMARY OF THE INVENTION

The present invention relates to patient monitoring. Although embodiments make specific reference to monitoring impedance and electrocardiogram signals with an adherent patch, the system methods and device described herein may be applicable to any application in which physiological monitoring is used, for example wireless physiological monitoring for extended periods.

In many embodiments, an adherent device comprises an adhesive patch with at least two electrodes and an accelerometer. The accelerometer can be used to determine an orientation of the at least two measurement electrodes on a patient, for example a measurement axis defined by the at least two electrodes. This use of the accelerometer and the at least two measurement electrodes can be particularly advantageous with patient monitoring for an extended period, for example when it is desirable to detect subtle changes in patient physiology and the adherent patch with electrodes is replaced. By determining the orientation of the electrodes of the patch on the patient, physiologic measurements with the at least two electrodes can be adjusted and/or corrected in response to the orientation of the patch on the patient. In many embodiments, the accelerometer may be oriented with respect to an electrode measurement axis in a predetermined configuration, which can facilitate determination of the electrode measurement axis in response to the accelerometer signal. In many embodiments, the adherent patch and/or electrodes are replaced with a second adherent patch and/or electrodes, and the orientation of the second adherent patch and/or electrodes determined with the accelerometer or a second accelerometer. The determined orientation of the second patch and/or electrodes on the patient can be used to correct measurements made with the second adherent patch and/or electrodes, such that errors associated with the alignment of the first and second patch on the patient can be minimized, even inhibited.

In a first aspect, embodiments of the present invention provide a method of monitoring a patient. An adherent device is adhered to a skin of the patient. The adherent device comprises an accelerometer and at least two measurement electrodes. The at least two measurement electrodes can be separated by a distance to define an electrode measurement axis. An accelerometer signal is measured when the device is adhered to the patient. An orientation of the electrode measurement axis on the patient is determined in response to the accelerometer signal.

In many embodiments, the accelerometer comprises at least one measurement axis sensitive to gravity aligned with the electrode measurement axis. The at least one accelerometer measurement axis can be configured to extend substantially horizontally on the patient when the device is adhered to the patient. The accelerometer signal may correspond to at least one accelerometer measurement vector in a direction along the at least one accelerometer measurement axis.

In many embodiments, the accelerometer comprises at least one accelerometer measurement axis sensitive to gravity, and the at least one accelerometer measurement axis is oriented with respect to the electrode measurement axis in a predetermined configuration.

The at least two electrodes may comprise a positive electrode and a negative electrode that define an orientation of an electrode measurement vector along the electrode measurement axis. The accelerometer signal may correspond to at least one accelerometer measurement vector that extends away from the electrode measurement axis. The at least one accelerometer measurement vector can be sensitive to gravity such that the accelerometer signal indicates when the patch adhered to the patient is upside down.

In many embodiments, the adherent device comprises an adherent surface to adhere to a skin of the patient, and electrode measurement axis extends along the adherent surface. The accelerometer may comprise three axes, and a first axis and a second axis of the three axes may extend along the measurement surface. A third axis of the three axes may extend away from the measurement surface.

In a specific embodiment, the accelerometer measurement signal may correspond to three orthogonal measurement vectors and each of the three orthogonal measurement vectors can extends along one of the accelerometer measurement axes.

In many embodiments, an electrocardiogram signal is measured with the at least two measurement electrodes, and the electrocardiogram signal is modified in response to the accelerometer signal. For example, the electrocardiogram vector can be rotated in response to the accelerometer signal to obtain a standard electrocardiogram vector. As a result of the rotation, the amplitude and direction of electrocardiogram features can be modified so as to approximate those of a standard electrocardiogram vector.

In another aspect, embodiments of the present invention provide a method of monitoring a patient. A first adherent patch is adhered to a skin of the patient, and the first patch comprises an adhesive and electrodes. A first accelerometer signal is measured when the first adherent patch is adhered to the patient. A second adherent patch is adhered to the skin of the patient, and the second patch comprises an adhesive and electrodes. A second accelerometer signal is measured when the second adherent patch is adhered to the patient. An orientation on the patient of at least one of the first patch or the second patch is determined in response to at least one of the first accelerometer signal or the second accelerometer signal.

In many embodiments, a first electrocardiogram signal is measured when the first adherent patch is adhered to the patient. A second electrocardiogram signal is measured when the second adherent patch is adhered to the patient. At least one of the first electrocardiogram signal or the second electrocardiogram signal is adjusted in response to at least one of the first accelerometer signal or the second accelerometer signal.

In another aspect, embodiments of the present invention provide a method of monitoring a patient. A first adherent measurement device is adhered to a skin of the patient. The first adherent measurement device comprises a first accelerometer and a first at least two measurement electrodes. A second adherent measurement device is adhered to a skin of the patient. The second adherent measurement device comprises a second accelerometer and a second at least two measurement electrodes. A first accelerometer signal is measured and a first electrocardiogram signal is measured with the first at least two measurement electrodes. The first accelerometer signal and the first electrocardiogram signal are measured when the first adherent measurement device is adhered to the skin of the patient. A second accelerometer signal is measured and a second electrocardiogram signal is measured with the second at least two measurement electrodes. The second accelerometer signal and the second electrocardiogram signal are measured when the second adherent measurement device is adhered to the skin of the patient. The first electrocardiogram signal is combined with the second electrocardiogram signal in response to the first accelerometer signal and the second accelerometer signal. The electrocardiogram signals can be combined by summing a scaled version of each signal.

In many embodiments, the first accelerometer comprises a first accelerometer measurement axis and the first at least two electrodes are separated by a first distance to define a first electrode measurement axis. The first accelerometer measurement axis can be aligned with the first electrode measurement axis. The second accelerometer may comprise a second accelerometer measurement axis and the second at least two electrodes can be separated by a second distance to define a second electrode measurement axis. The second accelerometer measurement axis may be aligned with the second electrode measurement axis.

In many embodiments, an orientation of the first electrode measurement axis is determined in response to the first accelerometer signal. An orientation of the second electrode measurement axis is determined in response to the to the accelerometer signal.

In many embodiments, the first electrocardiogram signal is combined with the second electrocardiogram signal when the second adherent measurement device is adhered to the skin of the patient.

In another aspect, embodiments of the present invention provide a device for monitoring a patient. The device comprises a support with an adhesive to adhere to a skin of the patient, and an accelerometer to generate an accelerometer signal with the accelerometer supported with the support. At least two measurement electrodes are supported with the support, and the at least two measurement electrodes are separated by a distance to define an electrode measurement axis. The device comprises circuitry to measure the accelerometer signal when the device is adhered to the patient. A processor comprises a tangible medium configured to determine an orientation of the electrode measurement axis on the patient in response to the accelerometer signal.

In many embodiments, the support comprises an adhesive patch with an adhesive to adhere the support, to the patient. The adhesive patch may comprise a breathable tape with adhesive to adhere the support to the patient.

In many embodiments, the accelerometer comprises at least one measurement axis sensitive to gravity aligned with the electrode measurement axis. The accelerometer may comprise at least one accelerometer measurement axis sensitive to gravity, and the accelerometer may be positioned and supported with the support such that the measurement axis extends substantially horizontally on the patient when the support is adhered to the patient.

In many embodiments, the accelerometer signal corresponds to at least one accelerometer measurement vector along the at least one accelerometer measurement axis.

In many embodiments, the accelerometer comprises at least one accelerometer measurement axis sensitive to gravity, and the at least one accelerometer measurement axis is oriented with respect to the electrode measurement axis in a predetermined configuration. The at least two electrodes may comprise a positive electrode and a negative electrode that define an orientation of an electrode measurement vector along the electrode measurement axis.

In many embodiments, the accelerometer signal corresponds to at least one measurement vector that extends away from the electrode measurement axis such that the accelerometer signal indicates when the patch adhered to the patient is upside down.

In many embodiments, the adherent device comprises an adherent surface to adhere to a skin of the patient, and the electrode measurement axis extends along the adherent surface. The accelerometer may comprise three axes, and a first axis and a second axis of the three axes can extend along the adherent surface. A third axis of the three axes can extend away from the adherent surface.

In many embodiments, the accelerometer signal corresponds to three orthogonal measurement vectors, and each of the three orthogonal measurement vectors extends along one of the accelerometer measurement axes.

In many embodiments, measurement circuitry is coupled to the at least two measurement electrode to measure an electrocardiogram signal. A processor is coupled to the measurement circuitry and comprises a tangible medium configured to modify the electrocardiogram signal in response to the accelerometer signal.

In another aspect, embodiments of the present invention provide a system for monitoring a patient. The system comprises a first support, with a first adhesive to adhere to a skin of the patient. First electrodes are supported with the support to couple to the skin of the patient. The system comprises a second support with a second adhesive to adhere to the skin of the patient. Second electrodes are supported with the second support to couple to the skin of the patient. At least one accelerometer is coupled to at least one of the first support or the second support to determine an orientation of at least one of the first electrodes or the second electrodes when the at least one of the first electrodes or the second electrodes are coupled to the patient.

In many embodiments, the at least one accelerometer comprises a first accelerometer removably coupled to the first support in a first predetermined orientation and a second accelerometer removably coupled to the second support in a second predetermined orientation.

In many embodiments, the at least one accelerometer comprises an accelerometer removably coupled to the first support in a first predetermined orientation and wherein the accelerometer is removably coupled to the second support in a second predetermined orientation such that the accelerometer can be reused.

In many embodiments, the first support with the first adhesive comprises a first breathable tape and the second support with the second adhesive comprises a second breathable tape.

In another aspect, embodiments of the present invention provide a system for monitoring a patient. The system comprises a first adherent measurement device comprising a first support with a first adhesive to adhere the first support to a skin of the patient. The first adherent measurement device comprises a first accelerometer and a first at least two measurement electrodes. The first adherent device comprises first measurement circuitry to measure a first accelerometer signal with the accelerometer and a first electrocardiogram signal with the first at least two measurement electrodes. A second adherent measurement device comprises a second support with a second adhesive to adhere the second support to a skin of the patient. The second adherent measurement device comprises a second accelerometer and a second at least two measurement electrodes. The second accelerometer comprises second circuitry to measure a second accelerometer signal with the second accelerometer and a second electrocardiogram signal with the second at least two measurement electrodes. A processor system comprises a tangible medium configured to combine the first electrocardiogram signal with the second electrocardiogram signal in response to the first accelerometer signal and the second accelerometer signal.

In many embodiments, the first accelerometer comprises a first accelerometer measurement axis and the first at least two electrodes are separated by a first distance to define a first electrode measurement axis. The first accelerometer measurement axis is aligned with the first electrode measurement axis. The second accelerometer comprises a second accelerometer measurement axis and the second at least two electrodes are separated by a second distance to define a second electrode measurement axis. The second accelerometer measurement axis may be aligned with the second electrode measurement axis. The processor system can be configured to determine an orientation of the first electrode measurement axis in response to the first accelerometer signal and determine an orientation of the second electrode measurement axis in response to the to the accelerometer signal.

The processor system may comprise at least one processor supported with at least one of the first support or the second support, and the at least one processor can be configured to combine the first electrocardiogram signal with the second electrocardiogram signal in response to the first accelerometer signal and the second accelerometer signal. Combining may include scaling each signal and summing the signals together.

BRIEF DESCRIPTION OF THE DRAWINGS

FIG. 1D shows a printed circuit boards and electronic components over the adherent patch, as in FIG. 1C;

FIG. 1D1 shows an equivalent circuit that can be used to determine optimal frequencies for determining patient hydration, according to embodiments of the present invention;

FIG. 1D2 shows an adherent devices as in FIGS. 1A-1D positioned on a patient to determine orientation of the adherent patch on the patient, according to embodiments of the present invention;

FIG. 1D3 shows vectors from a 3D accelerometer to determine orientation of the measurement axis of the patch adhered on the patient, according to embodiments of the present invention;

FIGS. 1I and 1J show a side cross-sectional view and an exploded view, respectively, of the adherent device as in FIGS. 1A to 1H;

FIG. 1K shows at least one electrode configured to electrically couple to a skin of the patient through a breathable tape, according to embodiments of the present invention;

DETAILED DESCRIPTION OF THE INVENTION

Embodiments of the present invention relate to patient monitoring. Although embodiments make specific reference to monitoring impedance and electrocardiogram signals with an adherent patch, the system methods and device described herein may be applicable to any application in which physiological monitoring is used, for example wireless physiological monitoring for extended periods.

In many embodiments, an adherent device comprises an adhesive patch with at least two electrodes and an accelerometer. The accelerometer can be used to determine an orientation of the at least two measurement electrodes on a patient, for example a measurement axis defined by the at least two electrodes. This use of the accelerometer and the at least two measurement electrodes can be particularly advantageous with patient monitoring for an extended period, for example when it is desirable to detect subtle changes in patient physiology and the adherent patch with electrodes is replaced. By determining the orientation of the electrodes of the patch on the patient, physiologic measurements with the at least two electrodes can be adjusted and/or corrected in response to the orientation of the patch on the patient. In many embodiments, the accelerometer may be oriented with respect to an electrode measurement axis in a predetermined configuration, which can facilitate determination of the electrode measurement axis in response to the accelerometer signal. In many embodiments, the adherent patch and/or electrodes are replaced with a second adherent patch and/or electrodes, and the orientation of the second adherent patch and/or electrodes determined with the accelerometer or a second accelerometer. The determined orientation of the second patch and/or electrodes on the patient can be used to correct measurements made with the second adherent patch and/or electrodes, such that errors associated with the alignment of the first and second patch on the patient can be minimized, even inhibited.

As used herein, an adhesive patch encompasses a piece of soft material with an adhesive that can cover a part of the body.

In many embodiments, the adherent devices described herein may be used for 90 day monitoring, or more, and may comprise completely disposable components and/or reusable components, and can provide reliable data acquisition and transfer. In many embodiments, the patch is configured for patient comfort, such that the patch can be worn and/or tolerated by the patient for extended periods, for example 90 days or more. In many embodiments, the adherent patch comprises a tape, which comprises a material, preferably breathable, with an adhesive, such that trauma to the patient skin can be minimized while the patch is worn for the extended period. In many embodiments, the printed circuit board comprises a flex printed circuit board that can flex with the patient to provide improved patient comfort.

Figure 1A:
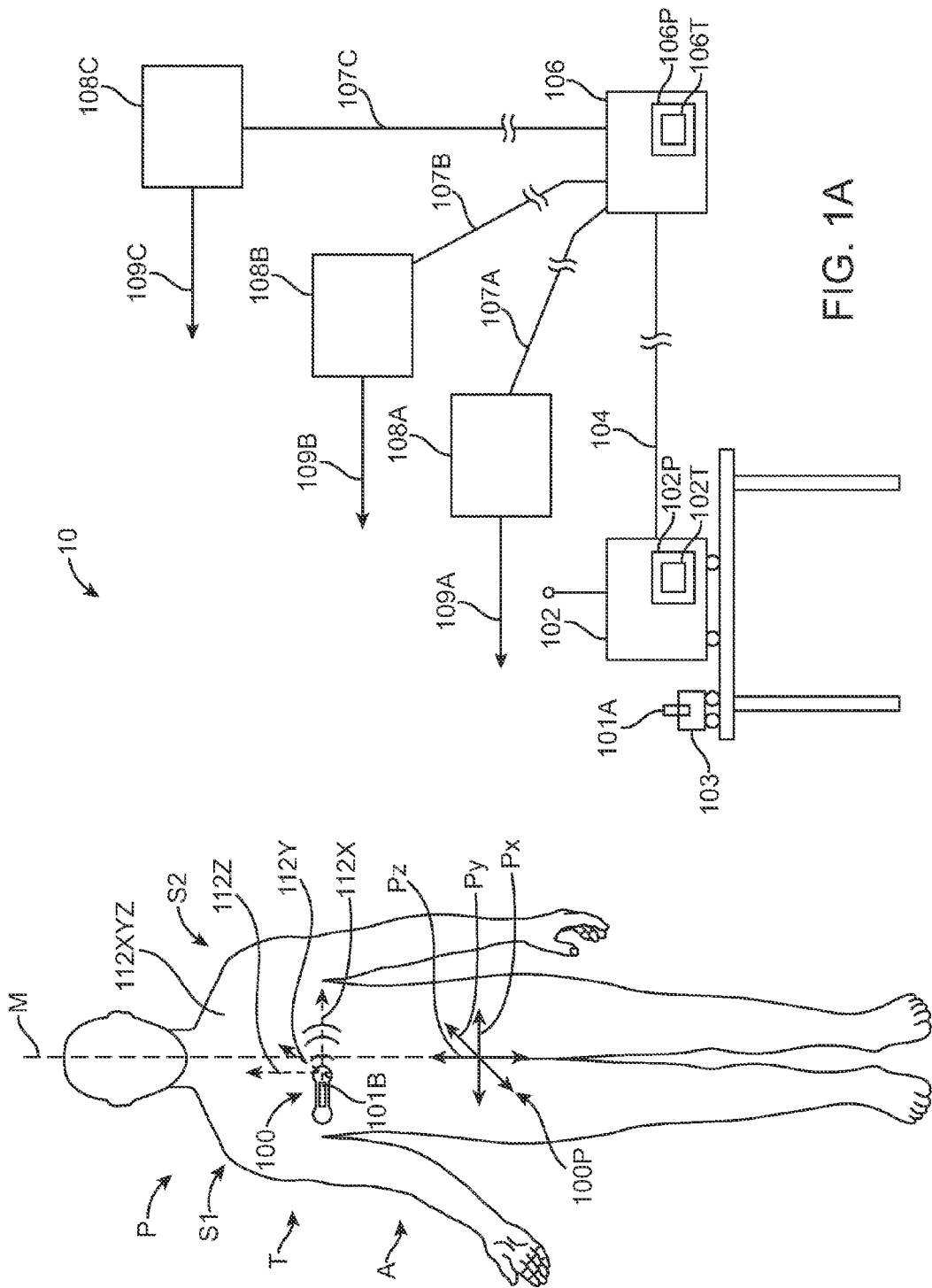
FIG. 1A shows a patient and a monitoring system comprising an adherent device, according to embodiments of the present invention.

FIG. 1A shows a patient P and a monitoring system 10. Patient P comprises a midline M, a first side S1, for example a right side, and a second side S2, for example a left side. Monitoring system 10 comprises an adherent device 100. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient.

Adherent device 100 can be aligned and/or oriented with respect to axes of patient P. Orientation of adherent device 100 can comprise orientation of device 100 with a patient coordinate system 100P aligned with axes of the patient. Patient P comprises a horizontal axis Px that extends laterally from one side of the patient to the other, for example from side S1 to side S1 across midline M. Patient P comprises an anterior posterior axis Py that extends from the front, or anterior, of the patient to the back, or posterior of the patient. Patient P comprises a vertical axis Pz that extends vertically along the patient, for example vertically along the midline of the patient from the feet of the patient toward the head of the patient. In many embodiments, horizontal axis Px, anterior posterior axis Py and vertical axis Pz may comprise a right handed triple of orthogonal coordinate references.

Adherent device 100 may comprise a 3D coordinate reference system 112XYZ. Device 100 may comprise an X-axis 112X for alignment with horizontal axis Px of the patient, a Y-axis for alignment with anterior posterior axis Py of the patient and a Z axis for alignment with vertical axis Pz of the patient. Coordinate reference system 112XYZ may comprise X-axis 112X, Y-axis 112Y and Z-axis 112Z. Coordinate reference system 112XYZ may comprise a right handed triple, although other non-orthogonal and orthogonal reference systems may be used.

Adherent device 100 may comprise indicia for alignment with an axis of the patient. The indicia can be used to align at least one axis of device 100 with at least one axis of the patient. The indicia, can be positioned on at least one of the adherent patch, a cover, or an electronics module. The indicia can be visible to the patient and or a care provider to adhere device 100 to the patient in alignment with at least one axis of the patient. A vertical line along Z-axis 112Z can indicate vertical axis 112Z to the patient and/or care provider, and a horizontal line along X-axis 112X can indicate horizontal X-axis 112X to the patient and/or care provider. A name, logo and/or trademark can be visible the outside of device 100 to indicate that device 100 correctly oriented, and arrows can also be used, for example a vertical arrow pointing up and a horizontal arrow pointing to the right.

Monitoring system 10 includes components to transmit data, to a remote center 106. Remote center 106 can be located in a different building from the patient, for example in the same town as the patient, and can be located as far from the patient as a separate continent from the patient, for example the patient located on a first continent and the remote center located on a second continent. Adherent device 100 can communicate wirelessly to an intermediate device 102, for example with a single wireless hop from the adherent device on the patient to the intermediate device. Intermediate device 102 can communicate with remote center 106 in many ways, for example with an internet connection and/or with a cellular connection. In many embodiments, monitoring system 10 comprises a distributed processing system with at least one processor comprising a tangible medium of device 100, at least one processor 102P of intermediate device 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In some embodiments, remote center 106 receives the patient data and applies a patient evaluation algorithm, for example an algorithm to calculate the apnea hypopnea index. When a flag is raised, the center may communicate with the patient, hospital, nurse, and/or physician to allow for therapeutic intervention.

The adherent device may be affixed and/or adhered to the body in many ways. For example, with at least one of the following: an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches, and each of the replaceable patches may include a battery. The module may collect cumulative data for approximately 90 days and/or the entire adherent component (electronics+ patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the patient.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, hear rate variability (HRV), heart rate turbulence (HRT), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

The adherent device can wirelessly communicate with remote center 106. The communication may occur directly (via a cellular or Wi-Fi network), or indirectly through intermediate device 102. Intermediate device 102 may consist of multiple devices, which can communicate wired or wirelessly to relay data to remote center 106.

In many embodiments, instructions are transmitted from remote site 106 to a processor supported with the adherent patch on the patient, and the processor supported with the patient can receive updated instructions for the patient treatment and/or monitoring, for example while worn by the patient.

Figure 1B:
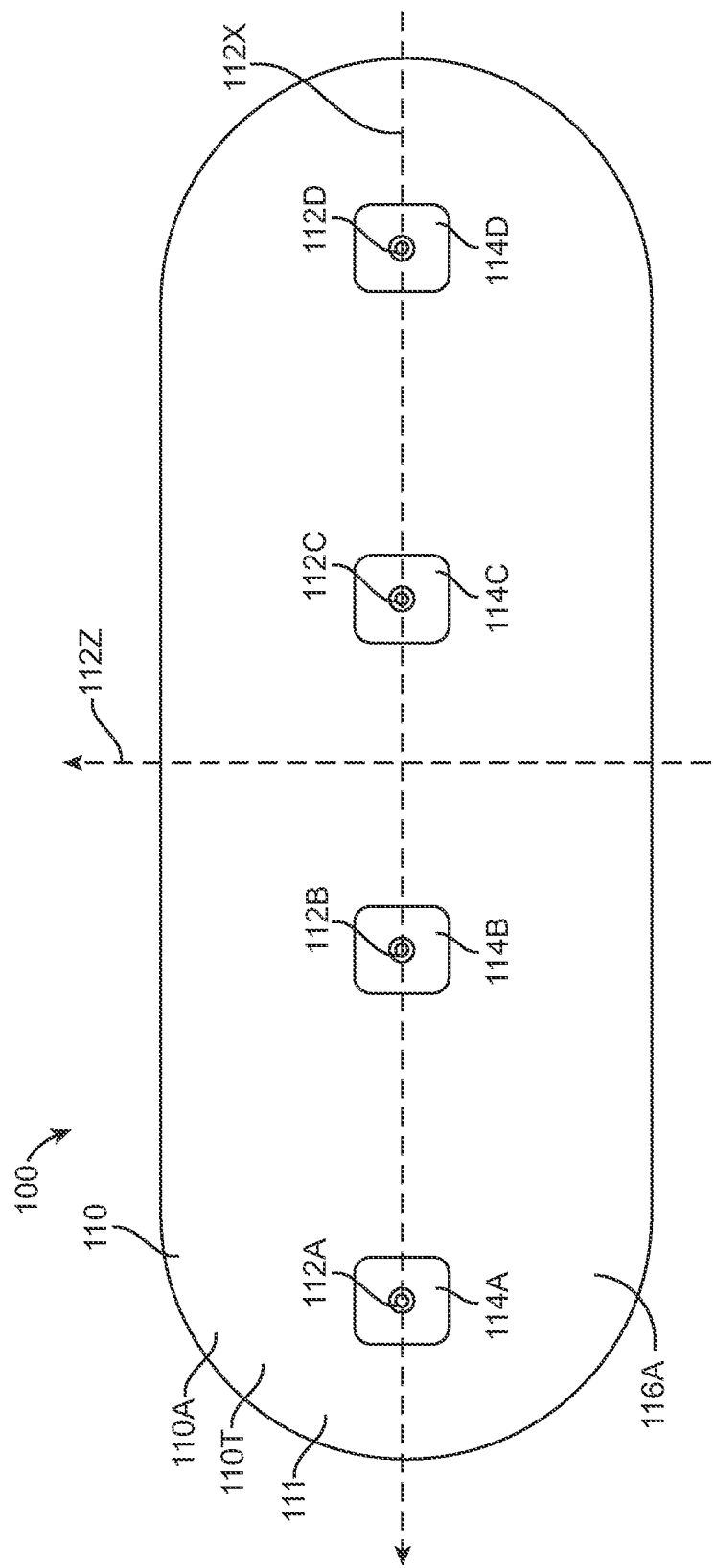
FIG. 1B shows a bottom view of the adherent device as in FIG. 1A comprising an adherent patch.

FIG. 1B shows a bottom view of adherent device 100 as in FIG. 1A comprising an adherent patch 110. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Electrodes 112A, 112B, 112C and 112D extend substantially along a horizontal measurement axis that corresponds to X axis-112X of the measurement device. Electrodes 112, 112B, 112C and 112D can be affixed to adherent patch 110A, such that the positions of electrodes 112A, 112B, 112C and 112D comprise predetermined positions on adherent patch 110A. Z-axis 112Z can extend perpendicular to the electrode measurement axis, for example vertically and perpendicular to X-axis 112 when adhered on the patient. X-axis 112X and Z-axis 112Z can extend along an adhesive surface of adherent patch 110A, and a Y-axis 112Y can extend away from the adhesive surface of adherent device 110A.

Figure 1C:
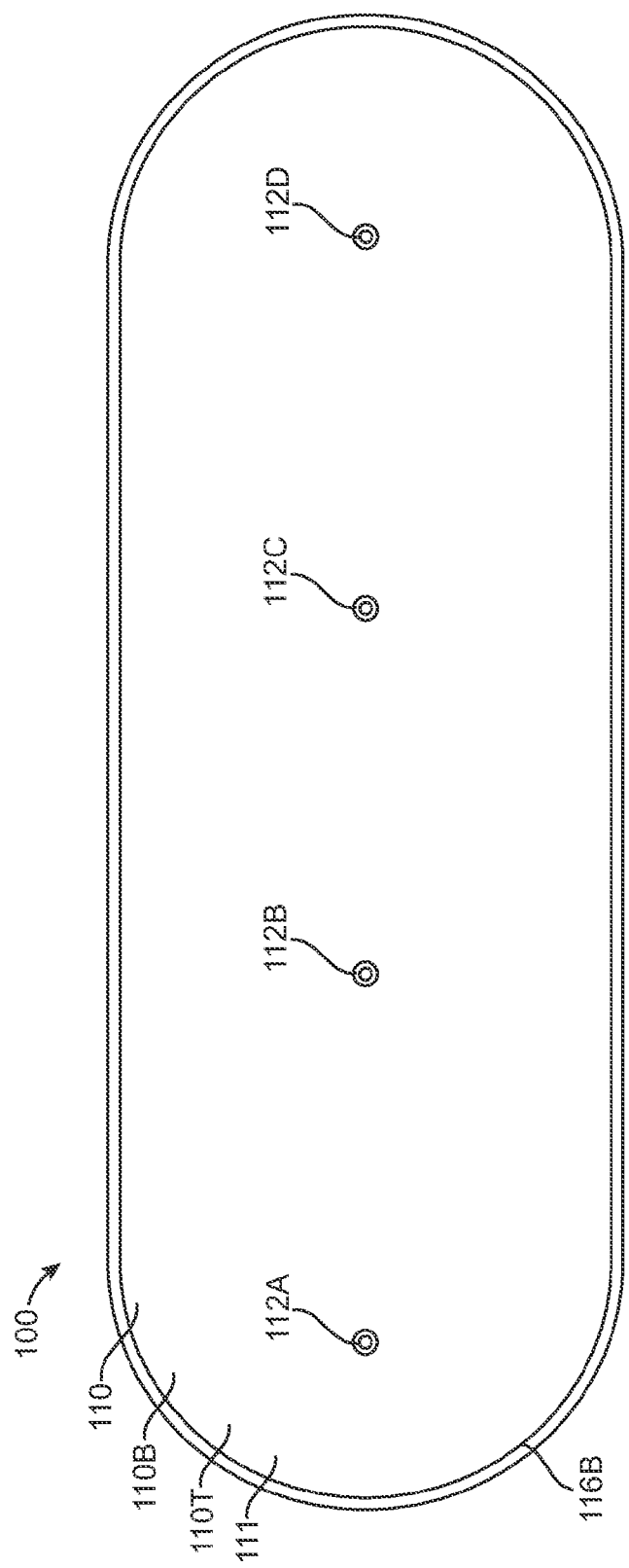
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient. The PCB may comprise completely flex PCB, rigid PCB, rigid PCB combined flex PCB and/or rigid PCB boards connected by cable.

FIG. 1D shows a printed circuit boards and electronic components over adherent patch 110, as in FIG. 1A to 1C. In some embodiments, a printed circuit board (PCB), for example flex printed circuit board 120, may be connected to electrodes 112A, 112B, 112C and 112D with connectors 122A, 122B, 122C and 122D. Flex printed circuit board 120 can include traces 123A, 123B, 123C and 123D that extend to connectors 122A, 122B, 122C and 122D, respectively, on the flex PCB. Connectors 122A, 122B, 122C and 122D can be positioned on flex printed circuit board 120 in alignment with electrodes 112A, 112B, 112C and 112D so as to electrically couple the flex PCB with the electrodes. For example, connectors 122A and 122D may comprise a flexible polyester film coated with conductive silver ink. In some embodiments, connectors 122A, 122B, 122C and 122D may comprise insulated wires and/or a film with conductive ink that provide strain relief between the PCB and the electrodes. In some embodiments, additional PCB's, for example rigid PCB's 120A, 120B, 120C and 120D, can be connected to flex printed circuit board 120. Electronic components 130 can be connected to flex printed circuit board 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles.

Electronics circuitry 130 may comprise a temperature sensor, for example a thermistor in contact with the skin of the patient, and temperature sensor circuitry 144 to measure a temperature of the patient, for example a temperature of the skin of the patient. A temperature sensor may be used to determine the sleep and wake state of the patient. The temperature of the patient can decrease as the patient goes to sleep and increase when the patient wakes up.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vaso-dilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Processor 146 may comprise many known processors with real time clock and frequency generator circuitry, for example the PIC series of processors available from Microchip, of Chandler Ariz. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, Zigbee, WiFi, WiMax, IR, amplitude modulation or frequency modulation. In many embodiments, the communications protocol comprises a two way protocol such that the remote center is capable of issuing commands to control data collection.

Intermediate device 102 may comprise a data collection system to collect and store data from the wireless transmitter. The data collection system can be configured to communicate periodically with the remote center. The data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprise a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or bioimpedance data, for example a respiration rate of the patient.

Activity sensor 134 may comprise an accelerometer with at least one measurement axis, for example two or more measurement axes. In some embodiments, activity sensor 134 comprises three axis accelerometer 134A. Three axis accelerometer 134A may comprise an X-axis 134X, a Y-axis 134Y and a Z-axis 134Z with each axis sensitive to gravity such that the orientation of the accelerometer can be determined in relation to gravity. Three axis accelerometer 134A can be aligned with electrodes of adherent patch 110A. X-axis 134X can be aligned with X-axis 112X of adherent patch 110. Y-axis 134Y can be aligned with Y-axis 112Y of adherent patch 110, Z-axis 134Z can be aligned with Z-axis 112Z of adherent patch 110. Axes of accelerometer 134A can be aligned with axes of patch 110A, for example with connectors 122A, 122B, 122C and 122D, such that the axes of the accelerometer are aligned with adherent patch and/or the electrodes in a predetermined configuration. Although the axes of the patch and accelerometer are shown substantially parallel, the axes of the patch can be aligned with the axes of the accelerometer in a non-parallel configuration, for example an oblique configuration with oblique angles between axes of the accelerometer and axes of the adherent patch and/or electrodes.

Impedance circuitry 136 can generate both hydration data and respiration data. In many embodiments, impedance circuitry 136 is electrically connected to electrodes 112A, 112B, 112C and 112D in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112B may comprise sense electrodes. The voltage measured by the sense electrodes can be used to measure the impedance of the patient and determine the respiration rate and/or hydration of the patient.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In some embodiments, ECG circuitry 138 can be connected to electrodes 112A and 112D so as to increase spacing of the electrodes. The inner electrodes may be positioned near the outer electrodes to increase the voltage of the ECG signal measured by ECG circuitry 138. In many embodiments, the ECG circuitry may measure the ECG signal from electrodes 112A and 112D when current is not passed through electrodes 112A and 112D.

ECG circuitry 138 can be coupled to the electrodes in many ways to define an electrocardiogram vector. For example electrode 112A can be coupled to a positive amplifier terminal of ECG circuitry 138 and electrode 112D can be coupled to a negative amplifier terminal of ECG circuitry 138 to define an orientation of an electrocardiogram vector along the electrode measurement axis. To define an electrocardiogram vector with an opposite orientation electrode 112D can be couple to the positive amplifier terminal of ECG circuitry 138 and electrode 112A can be coupled to the negative amplifier terminal of ECG circuitry 138. The ECG circuitry may be coupled to the inner electrodes so as to define an ECG vector along a measurement axis of the inner electrodes.

FIG. 1D2 shows adherent device 100 positioned on patient P to determine orientation of the adherent patch. X-axis 112X of device 100 is inclined at an angle α to horizontal axis Px of patient P. Z-axis 112Z of device 100 is inclined at angle α to vertical axis Pz of patient P. Y-axis 112Y may be inclined at a second angle, for example β, to anterior posterior axis Py and vertical axis Pz. As the accelerometer of adherent device 100 can be sensitive to gravity, inclination of the patch relative to axis of the patient can be measured, for example when the patient stands.

Figures 3A, 3B, 3C, 3D:
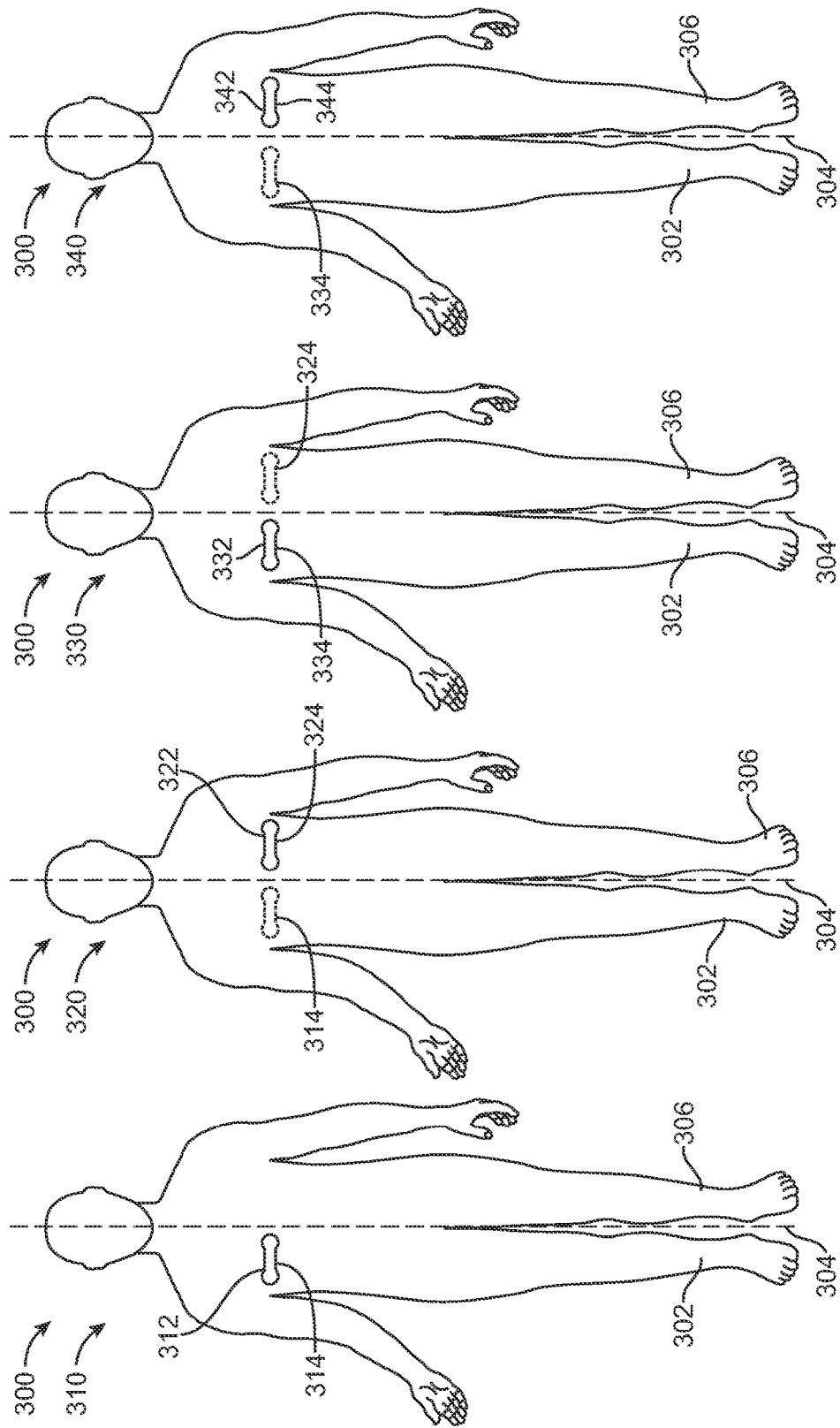
FIGS. 3A to 3D show a method of monitoring a patient for an extended period with an adherent patch with adherent patches alternatively adhered to the right side or the left side of the patient.

FIG. 1D3 shows vectors from a 3D accelerometer to determine orientation of the measurement axis of the patch adhered on the patient. A Z-axis vector 112ZV can be measured along vertical axis 112Z with an accelerometer signal from axis 134Z of accelerometer 134A. An X-axis vector 112XV can be measured along horizontal axis 112X with an accelerometer signal from axis 134X of accelerometer 134A. Inclination angle α can be determined in response to X-axis vector 112XV and Z-axis vector 112ZV, for example with vector addition of X-axis vector 112XV and Z-axis vector 112ZV. An inclination angle β for the patch along the Y and Z axes can be similarly obtained an accelerometer signal from axis 134Y of accelerometer 134A and vector 112ZV.

Figure 1E:
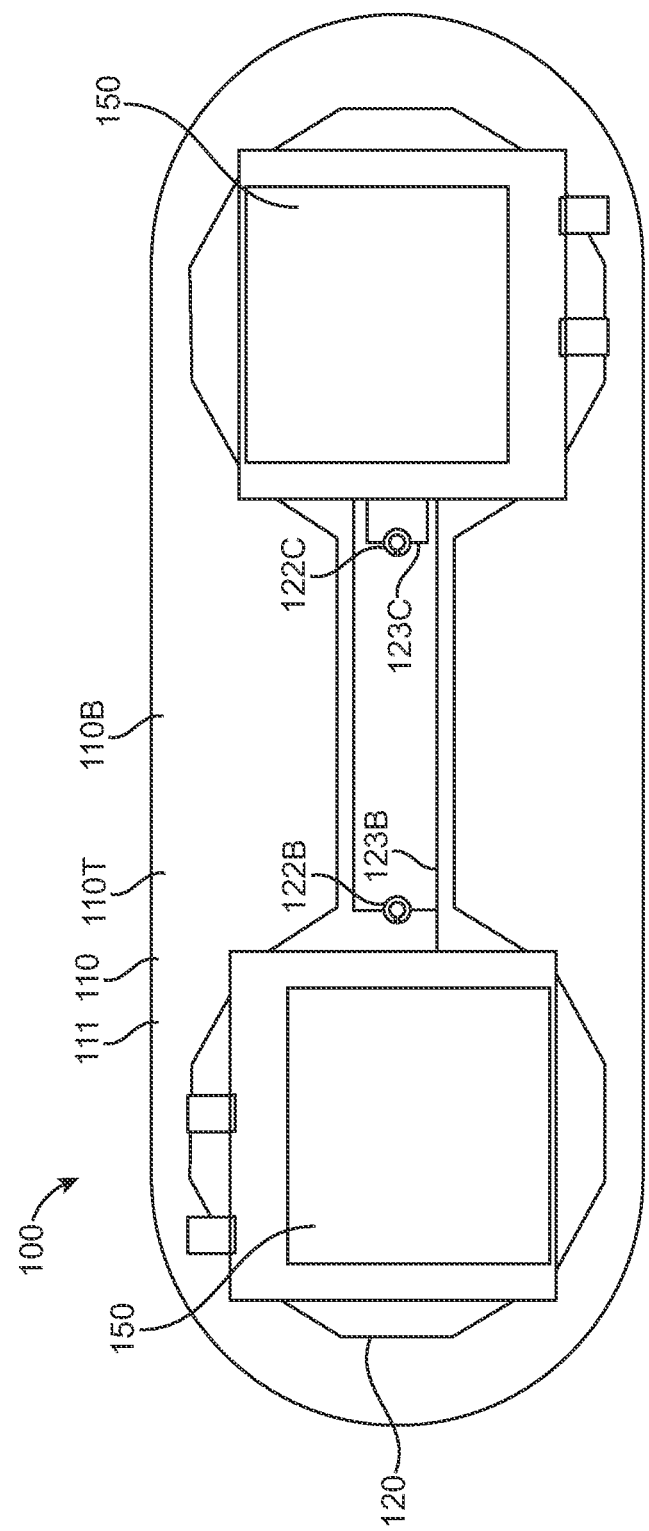
FIG. 1E shows batteries positioned over the printed circuit board and electronic components as in FIG. 1D.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
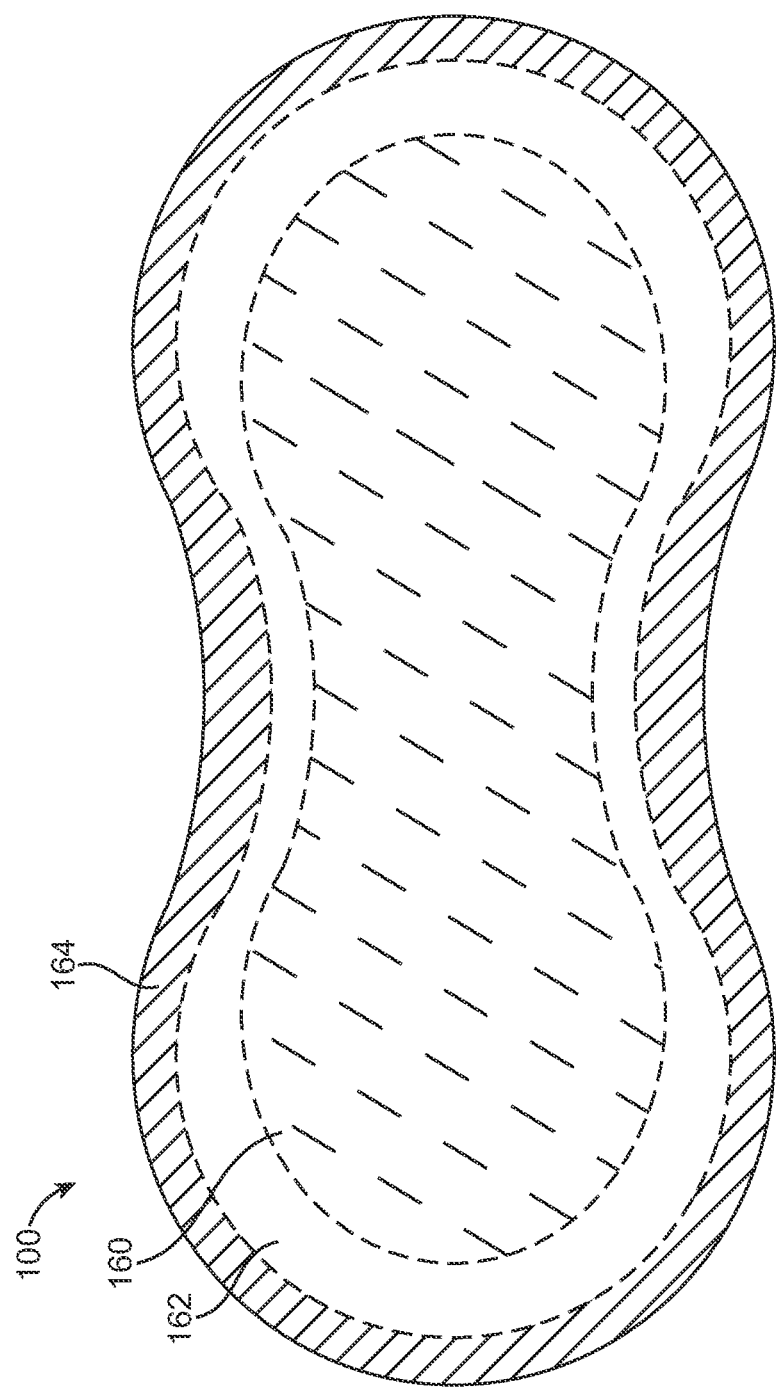
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIGS. 1A to 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adherent patch 110 with an adhesive 164 on an underside of cover 162. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, and/or elastane (Spandex). The breathable fabric may be coated to make it water resistant, waterproof, and/or to aid in wicking moisture away from the patch.

Figure 1H:
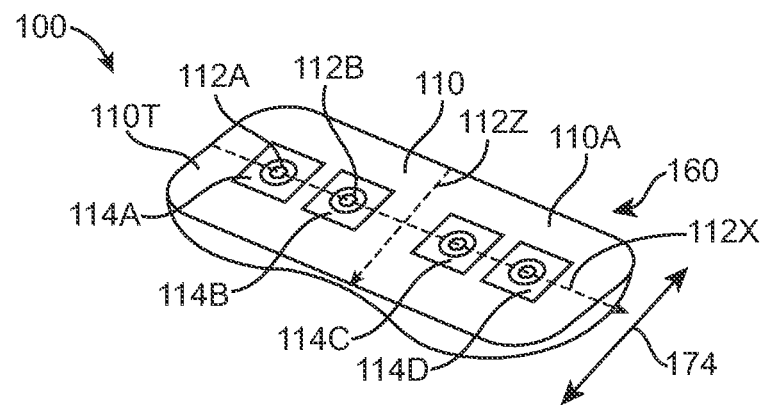
FIG. 1H shown a bottom isometric view of the adherent device as in FIGS. 1A to 1G.
Figure 1G:
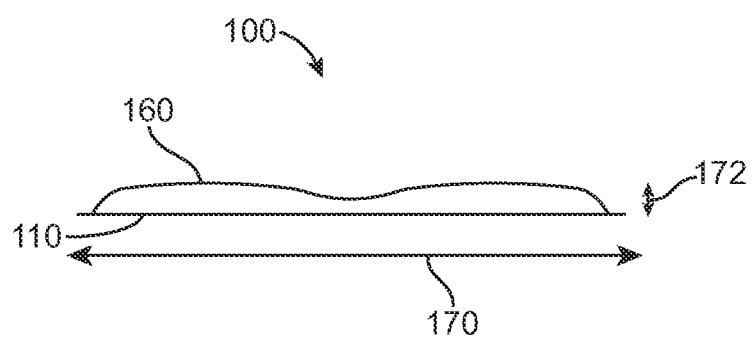
FIG. 1G shows a side view of the adherent device as in FIGS. 1A to 1F.

FIG. 1G shows a side view of adherent device 100 as in FIGS. 1A to 1F. Adherent device 100 comprises a maximum dimension, for example a length 170 from about 2 to 10 inches (from about 50 mm to about 250 mm), for example from about 4 to 6 inches (from about 100 mm to about 150 mm). In some embodiments, length 170 may be no more than about 6 inches (no more than about 150 mm). Adherent device 100 comprises a thickness 172. Thickness 172 may comprise a maximum thickness along a profile of the device. Thickness 172 can be from about 0.1 inches to about 0.4 inches (from about 5 mm to about 10 mm), for example about 0.3 inches (about 7.5 mm).

FIG. 1H shown a bottom isometric view of adherent device 100 as in FIGS. 1A to 1G. Adherent device 100 comprises a width 174, for example a maximum width along a width profile of adherent device 100. Width 174 can be from about 1 to about 4 inches (from about 25 mm to 100 mm), for example about 2 inches (about 50 mm).

Figure 1J:
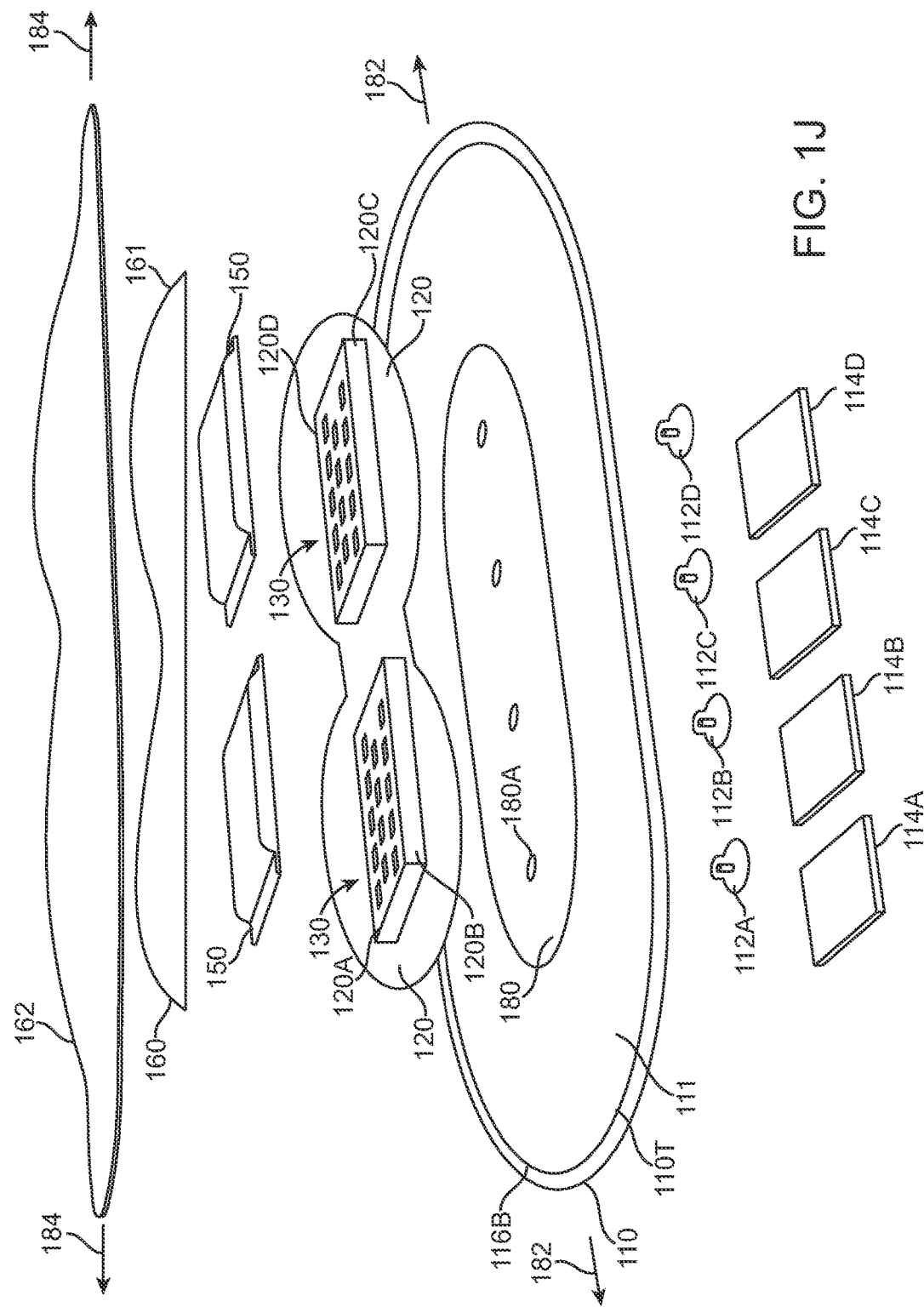

FIGS. 1I and 1J show a side cross-sectional view and an exploded view, respectively, of adherent device 100 as in FIGS. 1A to 1H. Device 100 comprises several layers. Gel 114A, or gel layer, is positioned on electrode 112A to provide electrical conductivity between the electrode and the skin. Electrode 112A may comprise an electrode layer. Adhesive patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of adherent patch 110. A gel cover 180, or gel cover layer, for example a polyurethane non-woven tape, can be positioned over patch 110 comprising the breathable tape. A PCB layer, for example flex printed circuit board 120, or flex PCB layer, can be positioned over gel cover 180 with electronic components 130 connected and/or mounted to flex printed circuit board 120, for example mounted on flex PCB so as to comprise an electronics layer disposed on the flex PCB layer. In many embodiments, the adherent device may comprise a segmented inner component, for example the PCB may be segmented to provide at least some flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex printed circuit board 120, so as to provide strain relive between the electrodes 112A, 112B, 112C and 112D and the PCB. Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture, for example liquid water, from penetrating though the gel cover into gel 114A while allowing moisture vapor from the gel, for example moisture vapor from the skin, to transmit through the gel cover. In many embodiments, cover 162 can encase the flex PCB and/or electronics and can be adhered to at least one of the electronics, the flex PCB or adherent patch 110, so as to protect at least the electronics components and the PCB. Cover 162 can attach to adhesive patch 110 with adhesive 116B. Cover 162 can comprise many known biocompatible cover materials, for example silicone. Cover 162 can comprise an outer polymer cover to provide smooth contour without limiting flexibility. In many embodiments, cover 162 may comprise a breathable fabric. Cover 162 may comprise many known breathable fabrics, for example breathable fabrics as described above. In some embodiments, the breathable cover may comprise a breathable water resistant cover. In some embodiments, the breathable fabric may comprise polyester, nylon, polyamide, and/or elastane (Spandex) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

The breathable cover 162 and adherent patch 110 comprises breathable tape can be configured to couple continuously for at least one week the at least one electrode to the skin so as to measure breathing of the patient. The breathable tape may comprise the stretchable breathable material with the adhesive and the breathable cover may comprises a stretchable water resistant material connected to the breathable tape, as described above, such that both the adherent patch and cover can stretch with the skin of the patient. Arrows 182 show stretching of adherent patch 110, and the stretching of adherent patch can be at least two dimensional along the surface of the skin of the patient. As noted above, connectors 122A, 122B, 122C and 122D between PCS 130 and electrodes 112A, 112B, 112C and 112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient. Cover 162 can be attached to adherent patch 110 with adhesive 116B such that cover 162 stretches and/or retracts when adherent patch 110 stretches and/or retracts with the skin of the patient. For example, cover 162 and adhesive patch 110 can stretch in two dimensions along length 170 and width 174 with the skin of the patient, and stretching along length 170 can increase spacing between electrodes. Stretching of the cover and adhesive patch 110, for example in two dimensions, can extend the time the patch is adhered to the skin as the patch can move with the skin such that the patch remains adhered to the skin. Cover 162 can be attached to adherent patch 110 with adhesive 116B such that cover 162 stretches and/or retracts when adherent patch 110 stretches and/or retracts with the skin of the patient, for example along two dimensions comprising length 170 and width 174. Electronics housing 160 can be smooth and allow breathable cover 162 to slide over electronics housing 160, such that motion and/or stretching of cover 162 is slidably coupled with housing 160. The printed circuit board can be slidably coupled with adherent patch 110 that comprises breathable tape 110T, such that the breathable tape can stretch with the skin of the patient when the breathable tape is adhered to the skin of the patient. Electronics components 130 can be affixed to printed circuit board 120, for example with solder, and the electronics housing can be affixed over the PCB and electronics components, for example with dip coating, such that electronics components 130, printed circuit board 120 and electronics housing 160 are coupled together. Electronics components 130, printed circuit board 120, and electronics housing 160 are disposed between the stretchable breathable material of adherent patch 110 and the stretchable water resistant material of cover 160 so as to allow the adherent patch 110 and cover 160 to stretch together while electronics components 130, printed circuit board 120, and electronics housing 160 do not stretch substantially, if at all. This decoupling of electronics housing 160, printed circuit board 120 and electronic components 130 can allow the adherent patch 110 comprising breathable tape to move with the skin of the patient, such that the adherent patch can remain adhered to the skin for an extended time of at least one week, for example two or more weeks.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of printed circuit board 120 and electronic components 130, as indicated by arrows 186. Printed circuit board 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers.

The breathable tape of adhesive patch 110 may comprise a first mesh with a first porosity and gel cover 180 may comprise a breathable tape with a second porosity, in which the second porosity is less than the first porosity to minimize, and even inhibit, flow of the gel through the breathable tape. The gel cover may comprise a polyurethane film with the second porosity.

In many embodiments, the adherent device comprises a patch component and at least one electronics module. The patch component may comprise adhesive patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adhesive patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. Two electronics modules can be provided, such that one electronics module can be worn by the patient while the other is charged, as described above. Monitoring with multiple adherent patches for an extended period is described in U.S. Pat. App. No. 60/972,537, the full disclosure of which is incorporated herein by reference and may be suitable for combination with some embodiments of the present invention. Many patch components can be provided for monitoring over the extended period. For example, about 12 patches can be used to monitor the patient for at least 90 days with at least one electronics module, for example with two reusable electronics modules.

At least one electrode 112A can extend through at least one aperture 180A in the breathable tape 110 and gel cover 180.

In some embodiments, the adhesive patch may comprise a medicated patch that releases a medicament, such as antibiotic, beta-blocker, ACE inhibitor, diuretic, or steroid to reduce skin irritation. The adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin and electrode through the breathable tape, for example with the gel.

Figure 2A:
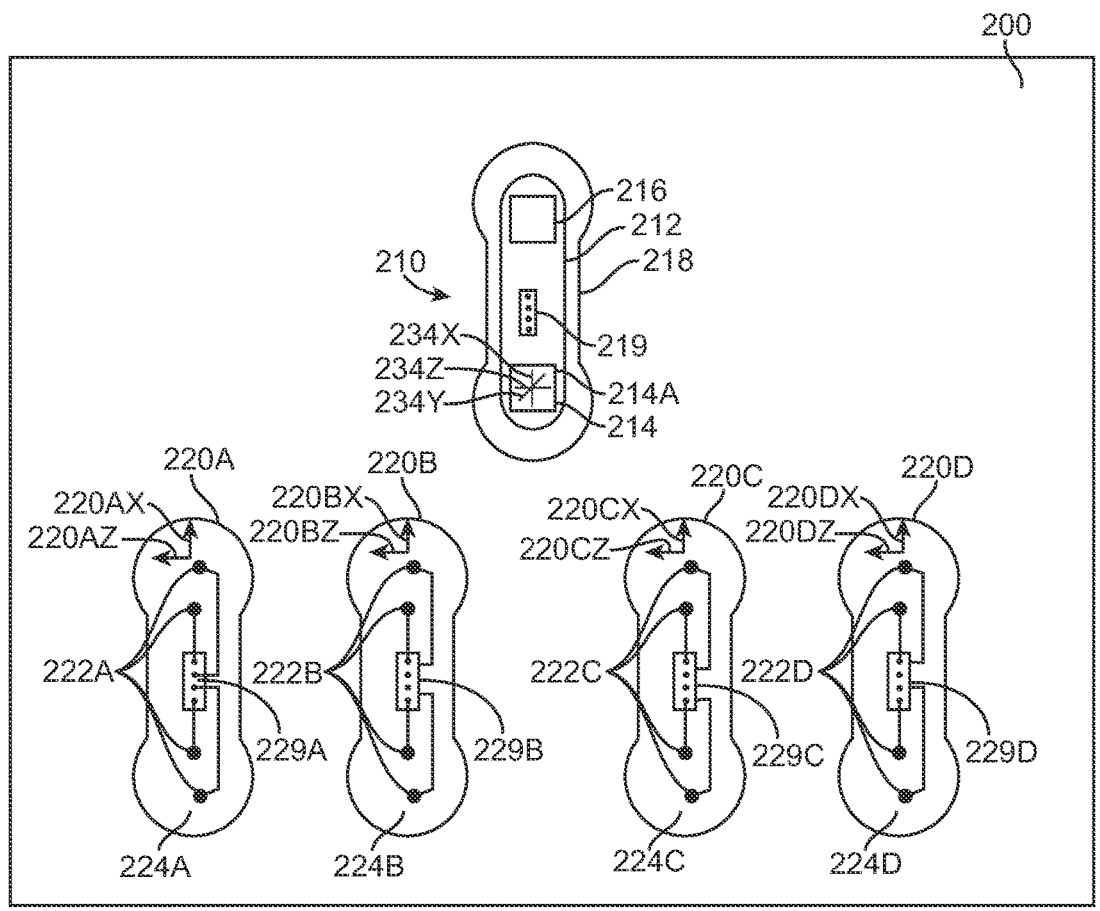
FIGS. 2A to 2C show a system to monitor a patient for an extended period comprising a reusable electronic component and a plurality of disposable patch components, according to embodiments of the present invention.
Figure 2B:
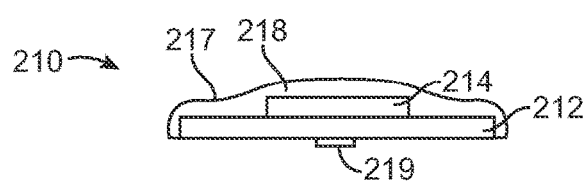
Figure 2C:
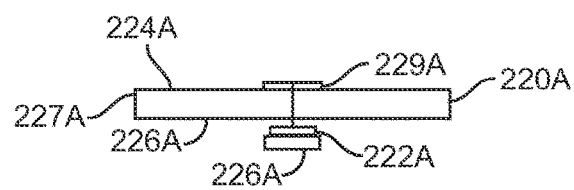

FIGS. 2A to 2C show a schematic illustration of a system 200 to monitor a patient for an extended period.

FIG. 2A shows a schematic illustration of system 200 comprising a reusable electronics module 210 and a plurality of disposable patch components. FIG. 2B shows a schematic illustration of a side cross-sectional view of reusable electronics module 210. System 200 may comprise a first disposable patch component 220A, a second disposable patch component 220B, a third disposable patch component 220C and a fourth disposable patch component 220D. Although four patch components a shown the plurality may comprise as few as two patch component and as many as three or more patch components, for example 25 patch components.

Reusable electronics module 210 may comprise a connector 219 adapted to connect to each of the disposable patch components, sequentially, for example one disposable patch component at a time. Connector 219 can be formed in many ways, and may comprise known connectors as described above, for example a snap. In some embodiments, the connectors on the electronics module and adhesive component can be disposed at several locations on the reusable electronics module and disposable patch component, for example near each electrode, such that each electrode can couple directly to a corresponding location on the flex PCB of the reusable electronics component.

Reusable electronics module 210 may comprise additional reusable electronics modules, for example two or more rechargeable electronics modules each with a 3D accelerometer, such that the first module comprising a first 3D accelerometer can be recharged while the second module comprising a second 3D accelerometer is worn by the patient. The second module can be recharged and connected to a third adhesive patch when the first adhesive patch is removed from the patient. The second module comprising the second accelerometer can be removably coupled to the adhesive patch such that the second accelerometer can be recharged and connected to a fourth adhesive patch when the second adhesive patch is removed from the patient.

Reusable electronics module 210 may comprises many of the structures described above that may comprise the electronics module. In many embodiments, reusable electronics module 210 comprises a PCB, for example a flex PCB 212, electronics components 214, batteries 216, and a cover 217, for example as described above. In some embodiments, reusable electronics module 210 may comprise an electronics housing over the electronics components and/or PCB as described above. The electronics components may comprise circuitry and/or sensors for measuring ECG signals, hydration impedance signals, respiration impedance signals and accelerometer signals, for example as described above.

Electronics components 214 may comprise an accelerometer 214A. Accelerometer 214A may comprise a three axis accelerometer, for example as described above. Accelerometer 214A may comprise an X-axis 234X, a Y-axis 234Y and a Z-axis 234Z with each axis sensitive to gravity such that the orientation of the accelerometer, for example 3D orientation, can be determined in relation to gravity, as described above. Alignment of the accelerometer, for example the axes of the accelerometer 214A, can be aligned with the axes of the adherent patches using the connectors. For example connector 219 can connect with at least one of connector 229A, connector 229B, connector 229C and connector 229D to align the respective patch with accelerometer 214A.

First disposable patch component 220A comprises a connector 229A to mate with connector 219 on reusable electronics module 210 such that the first disposable patch component 220A is aligned with the reusable electronics module with a predetermined orientation. First disposable patch component 220A comprises a first axis 220AX substantially aligned with electrodes 222A. A second axis 220AZ corresponds to vertical on the patient when first disposable patch component 220A is adhered to the patient. Connector 229A is configured to mate with connector 219 such that axis 234X is aligned with first axis 220AX and axis 234Z is aligned with axis 220AZ.

Second disposable patch component 220B comprises a connector 229B to mate with connector 219 on reusable electronics module 210 such that the second disposable patch component 220B is aligned with the reusable electronics module with the predetermined orientation similar to first disposable patch component 220A. Second disposable patch component 220B comprises a first axis 220BX substantially aligned with electrodes 222B. A second axis 220BZ corresponds to vertical on the patient when second disposable patch component 220B is adhered to the patient. Connector 229B is configured to mate with connector 219 such that axis 234X is aligned with first axis 220BX and axis 234Z is aligned with axis 220BZ.

Third disposable patch component 220C comprises a connector 229C to mate with connector 219 on reusable electronics module 210 such that the third disposable patch component 220C is aligned with the reusable electronics module with the predetermined orientation similar to second disposable patch component 220B. Third disposable patch component 220C comprises a first axis 220CX substantially aligned with electrodes 222C. A second axis 220CZ corresponds to vertical on the patient when second disposable patch component 220C is adhered to the patient. Connector 229C is configured to mate with connector 219 such that axis 234X is aligned with first axis 220CX and axis 234Z is aligned with axis 220CZ.

Fourth disposable patch component 220D comprises a connector 229D to mate with connector 219 on reusable electronics module 210 such that the fourth disposable patch component 220D is aligned with the reusable electronics module with the predetermined orientation similar to third disposable patch component 220C. Fourth disposable patch component 220D comprises a first axis 220DX substantially aligned with electrodes 222D. A second axis 220DZ corresponds to vertical on the patient when second disposable patch component 220D is adhered to the patient Connector 229D is configured to mate with connector 219 such that axis 234X is aligned with first axis 220DX and axis 234Z is aligned with axis 220DZ.

FIG. 2C shows a schematic illustration first disposable patch component 220A of the plurality of disposable patch components that is similar to the other disposable patch components, for example second disposable patch component 220B, third disposable patch component 220C and fourth disposable patch component 220C. The disposable patch component comprises a breathable tape 227A, an adhesive 226A on an underside of breathable tape 227A to adhere to the skin of the patient, and at least four electrodes 222A. The at least four electrodes 224A are configured to couple to the skin of a patient, for example with a gel 226A, in some embodiments the electrodes may extend through the breathable tape to couple directly to the skin of the patient with aid form the gel. In some embodiments, the at least four electrodes may be indirectly coupled to the skin through a gel and/or the breathable tape, for example as described above. A connector 229A on the upper side of the disposable adhesive component can be configured for attachment to connector 219 on reusable electronics module 210 so as to electrically couple the electrodes with the electronics module. The upper side of the disposable patch component may comprise an adhesive 224A to adhere the disposable patch component to the reusable electronics module. The reusable electronics module can be adhered to the patch component with many additional known ways to adhere components, for example with Velcro™ comprising hooks and loops, snaps, a snap fit, a lock and key mechanisms, magnets, detents and the like.

Figure 2D:
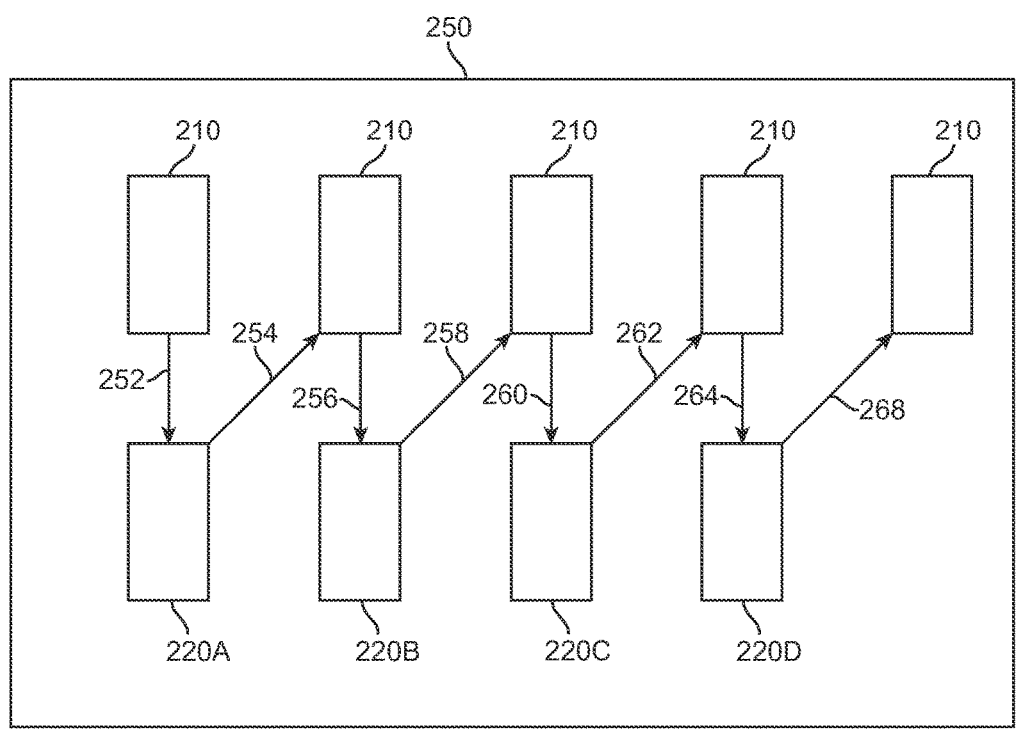
FIG. 2D shows a method of using the system as in FIGS. 2A to 2C.

FIG. 2D shows a method 250 of using system 200, as in FIGS. 2A to 2C. A step 252 adheres electronics module 210 to first disposable adherent patch component 220A of the plurality of adherent patch components and adheres the first disposable patch component to the skin of the patient, for example with the first adherent patch component adhered to the reusable electronics module. The orientation on the patient of first disposable patch component 220A is determined with the accelerometer, for example as described above, when the first disposable patch component is adhered to the patient. Patient measurements can be taken with the electronics module and/or adjusted in response to the orientation of the first patch on the patient. A step 254 removes the first disposable adherent patch from the patient and separates first disposable adherent patch component 220A from reusable electronics module 210.

A step 256 adheres electronics module 210 to second disposable adherent patch component 220B and adheres the second disposable patch component to the skin of the patient, for example with the second adherent patch component adhered to the reusable electronics module. The orientation on the patient of second disposable patch component 220B is determined with the accelerometer, for example as described above, when the second disposable patch component is adhered to the patient. Patient measurements can be taken with the electronics module and/or adjusted in response to the orientation of the second patch on the patient. A step 258 removes the second disposable adherent patch from the patient and separates second disposable adherent patch component 220B from reusable electronics module 210.

A step 260 adheres electronics module 210 to third disposable adherent patch component 220C and adheres the third disposable patch component to the skin of the patient, for example with the third adherent patch component adhered to the reusable electronics module. The orientation on the patient of third disposable patch component 220C is determined with the accelerometer, for example as described above, when the third disposable patch component is adhered to the patient. Patient measurements can be taken with the electronics module and/or adjusted in response to the orientation of the third patch on the patient. A step 262 removes the third disposable adherent patch from the patient and separates third disposable adherent patch component 220C from reusable electronics module 210.

A step 264 adheres electronics module 210 to fourth disposable adherent patch component 220D and adheres the fourth disposable patch component to the skin of the patient, for example with the third adherent patch component adhered to the reusable electronics module. The orientation on the patient of fourth disposable patch component 220D is determined with the accelerometer, for example as described above, when the fourth disposable patch component is adhered to the patient. Patient measurements can be taken with the electronics module and/or adjusted in response to the orientation of the fourth patch on the patient. A step 268 removes the fourth disposable adherent patch from the patient and separates fourth disposable adherent patch component 220D from reusable electronics module 210.

In many embodiments, physiologic signals, for example ECG, hydration impedance, respiration impedance and accelerometer impedance are measured when the adherent patch component is adhered to the patient, for example when any of the first, second, third or fourth disposable adherent patches is adhered to the patient.

FIGS. 3A to 3D show a method 300 of monitoring a patient for an extended period with adherent patches alternatively adhered to a right side 302 and a left side 304 of the patient. Work in relation to embodiments of the present invention suggests that repeated positioning of a patch at the same location can irritate the skin and may cause patient discomfort. This can be minimized, even avoided, by alternating the patch placement between left and right sides of the patient, often a front left and a front right side of the patient where the patient can reach easily to replace the patch. In some embodiments, the patch location can be alternated on the same side of the patient, for example higher and/or lower on the same side of the patient without substantial overlap to allow the skin to recover and/or heal. In many embodiments, the patch can be symmetrically positioned on an opposite side such that signals may be similar to a previous position of the patch symmetrically disposed on an opposite side of the patient. In many embodiments, the duration between removal of one patch and placement of the other patch can be short, such that any differences between the signals may be assumed to be related to placement of the patch, and these differences can be removed with signal processing.

In many embodiments each patch comprises at least four electrodes configured to measure an ECG signal and impedance, for example hydration and/or respiration impedance. In many embodiments, the patient comprises a midline 306, with first side, for example right side 302, and second side, for example left side 304, symmetrically disposed about the midline. A step 310 adheres a first adherent patch 312 to at a first location 314 on a first side 302 of the patient for a first period of time, for example about 1 week. When the adherent patch 312 is position at first location 314 on the first side of the patient, the accelerometer signals are measured to determine the orientation of the patch and the electrodes of the patch are coupled to the skin of the patient to measure the ECG signal and impedance signals.

A step 320 removes patch 312 and adheres a second adherent patch 322 at a second location 324 on a second side 206 of the patient for a second period of time, for example about 1 week. In many embodiments, second location 324 can be symmetrically disposed opposite first location 314 across midline 304, for example so as to minimize changes in the sequential impedance signals measured from the second side and first side. When adherent patch 322 is position at second location 324 on the second side of the patient, the orientation of the patch can be measured with the accelerometer and the electrodes of the patch are coupled to the skin of the patient to measure the ECG signal and impedance signals. In many embodiments, while adherent patch 322 is positioned at second location 324, skin at first location 314 can heal and recover from adherent coverage of the first patch. In many embodiments, second location 324 is symmetrically disposed opposite first location 314 across midline 304, for example so as to minimize changes in the impedance signals measured between the first side and second side. In many embodiments, the duration between removal of one patch and placement of the other patch can be short, such that any differences between the signals may be determined to be related to orientation of the patch, and these differences can be corrected in response to the measured orientation of the patch on the patient.

A step 330 removes second patch 322 and adheres a third adherent patch 332 at a third location 334 on the first side, for example right side 302, of the patient for a third period of time, for example about 1 week. In many embodiments, third location 334 can be symmetrically disposed opposite second location 324 across midline 304, for example so as to minimize changes in the sequential impedance signals measured from the third side and second side. In many embodiments, third location 334 substantially overlaps with first location 314, so as to minimize differences in measurements between the first adherent patch and third adherent patch that may be due to patch location. When adherent patch 332 is positioned at third location 334 on the first side of the patient, the orientation of the patch is measured with the accelerometer and the electrodes of the patch are coupled to the skin of the patient to measure the ECG signal and impedance signals. In many embodiments, while adherent patch 332 is positioned at third location 334, skin at second location 324 can heal and recover from adherent coverage of the second patch. In many embodiments, the duration between removal of one patch and placement of the other patch can be short, such that differences between the signals may be determined to be related to orientation of the patch, and these differences can be corrected in response to the measured orientation of the patch on the patient.

A step 340 removes third patch 332 and adheres a fourth adherent patch 342 at a fourth location 344 on the second side, for example left side 306, of the patient for a fourth period of time, for example about 1 week. In many embodiments, fourth location 344 can be symmetrically disposed opposite third location 334 across midline 304, for example so as to minimize changes in the sequential impedance signal measured from the fourth side and third side. In many embodiments, fourth location 344 substantially overlaps with second location 324, so as to minimize differences in measurements between the second adherent patch and fourth adherent patch that may be due to patch location. When adherent patch 342 is positioned at fourth location 344 on the second side of the patient, the orientation of patch is measured with the accelerometer and the electrodes of the patch are coupled to the skin of the patient to measure the ECG signal and impedance signals. In many embodiments, while adherent patch 342 is positioned at fourth location 324, skin at third location 334 can heal and recover from adherent coverage of the third patch. In many embodiments, the duration between removal of one patch and placement of the other patch can be short, such that differences between the signals may be determined to be related to orientation of the patch, and these differences can be corrected in response to the measured orientation of the patch on the patient.

The accelerometer signal measured to determine the orientation on the patient for each of adherent patch 312, adherent patch 322, adherent patch 332 or adherent patch 342 can be measured with a reusable accelerometer of a reusable electronics module, for example as described above, or measured with a disposable accelerometer affixed to each patch and disposed of with the patch after the patch is removed from the patient.

It should be appreciated that the specific steps illustrated in FIGS. 3A to 3D provide a particular method of monitoring a patient for an extended period, according to an embodiment of the present invention. Other sequences of steps may also be performed according to alternative embodiments. For example, alternative embodiments of the present invention may perform the steps outlined above in a different order. Moreover, the individual steps illustrated in FIGS. 3A to 3D may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 4A:
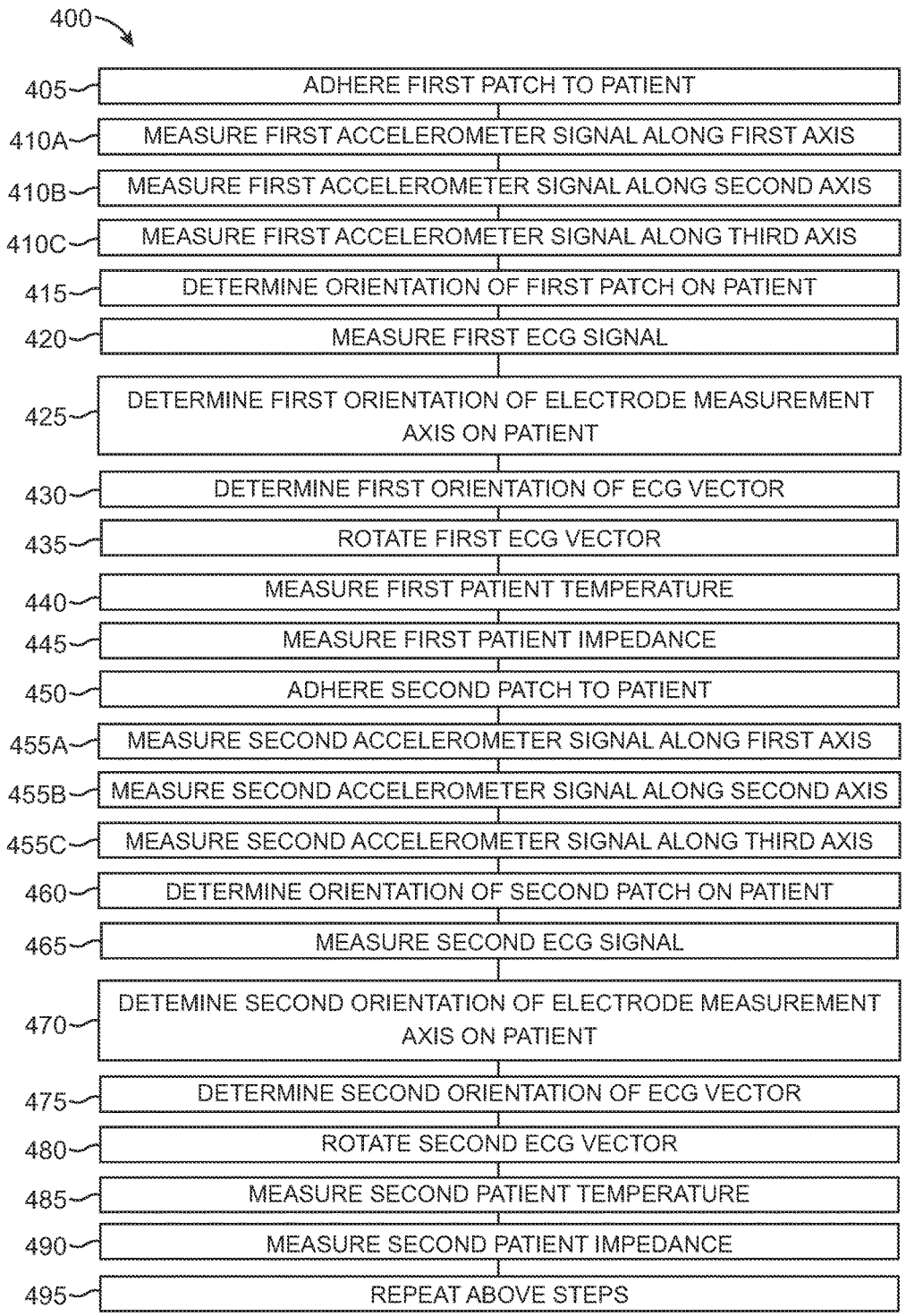
FIG. 4A shows a method of monitoring a patient, according to embodiments of the present invention.

FIG. 4A shows a method 400 of monitoring a patient. A step 405 adheres a first adherent patch to the patient, for example an adherent patch as described above. The first adherent patch may comprise a first patch that is separable from an electronics module, as described above. The first adherent patch may comprise a first patch of a first device with the electronics module fixed to the adherent patch, for example disposable electronics with a disposable patch.

A step 410A measures a first accelerometer signal along a first axis, for example an X-axis of a 3D accelerometer responsive to gravity as described above. A step 410B measures a first accelerometer signal along a second axis, for example a y-axis of a 3D accelerometer as described above. A step 410C measures a first accelerometer signal along a third axis, for example a Z-axis of a 3D accelerometer as described above. Measurement of the accelerometer signal with step 410A, step 410B and step 41C, which may comprise sub-steps, can be performed with the patient in a known and/or determined position. The patient may be asked to stand and/or sit upright in a chair and the first signal measured. In some embodiments, the 3D accelerometer signal can be analyzed to determine that the patient is standing, walking and the first signal determined from a plurality of measurements to indicate that the patient is upright for the measurement of the first signal.

A step 415 determines an orientation of the first patch on the patient. The accelerometer can be coupled to the patch with a pre-determined orientation, for example with connectors as described above, such that the orientation of the patch can be determined from the accelerometer signal and the orientation of the 3D accelerometer on the adherent patch and the orientation of the patient.

A step 420 measures a first ECG signal. The first ECG signal can be measured with the electrodes attached to the patient when the patch comprises the first orientation. The ECG signal can be measured with electronics components and electrodes, as described above.

A step 425 determines a first orientation of an electrode measurement axis on the patient. The electrode measurement axis may correspond to one of the measurement axes of the 3D accelerometer, for example an X-axis of the accelerometer as described above. However, the orientation of the electrode measurement axis can be aligned in relation to the axes of the accelerometer in many ways, for example at oblique angles, such that the alignment of the accelerometer with the electrode measurement axis is known and the signal from the accelerometer can be used to determine the alignment of the electrode measurement axis.

A step 430 determines a first orientation of the ECG vector. The orientation of the ECG vector can be determined in response to the polarity of the measurement electrodes and orientation of the electrode measurement axis, as described above.

A step 435 rotates a first ECG vector. The first ECG vector orientation of the ECG vector can be used to rotate the ECG vector onto a desired axis, for example an X-axis of the patient in response to the first orientation of the ECG vector and the accelerometer signal. For example, if the first measurement axis of the first ECG vector is rotated five degrees based on the accelerometer signal, the first ECG vector can be rotated by five degrees so as to align the first ECG vector with the patient axis.

A step 440 measures a first patient temperature. The first temperature of the patient can be measured with electronics of the adherent device, as described above.

A step 445 measures a first patient impedance. The first patient impedance may comprise a four pole impedance measurement, as described above. The first patient impedance can be used to determine respiration of the patient and/or hydration of the patient.

A step 450 adheres a second patch to the patient. The second patch may comprise a second patch connected to a reusable electronics module, for example a reusable electronics module connected to the first patch for the first patient measurements above. The second patch may comprise a second patch of a second adherent device comprising a second electronics module in which the second patch and second electronics module comprise a disposable second adherent device and the first adherent patch and first electronics module comprise a first disposable adherent device.

A step 455A measures a second accelerometer signal along a first axis, for example an x-axis of the accelerometer as described above. The first axis may comprise the first axis of the first accelerometer as described above, for example the X-axis of the accelerometer used to measure the X-axis signal with the first measurement. In some embodiments, the second accelerometer signal along the first axis may comprise an X-axis of a second accelerometer, for example a second disposable electronics module, aligned with an electrode measurement axis as described above.

A step 455B measures a second accelerometer signal along a second axis. The second axis may comprise the second axis of the first accelerometer as described above, for example the Y-axis of the accelerometer used to measure the Y-axis signal with the first measurement. In some embodiments, the second accelerometer signal along the second axis may comprise a Y-axis of a second accelerometer, for example a second disposable electronics module, aligned with an electrode measurement axis as described above.

A step 455C measures a second accelerometer signal along a third axis. The third axis may comprise the third axis of the first accelerometer as described above, for example the Z-axis of the accelerometer used to measure the Z-axis signal with the first measurement. In some embodiments, the second accelerometer signal along the third axis may comprise a Z-axis of a second accelerometer, for example a second disposable electronics module, aligned with an electrode measurement axis as described above.

A step 460 determines an orientation of the second patch on the patient. The accelerometer can be coupled to the second patch with a pre-determined orientation, for example with connectors as described above, such that the orientation of the second patch can be determined from the second accelerometer signal and the orientation of the 3D accelerometer on the adherent patch and the orientation of the patient.

A step 465 measures a second ECG signal. The second ECG signal can be measured with the electrodes attached to the patient when the second patch comprises the second orientation, for example after the first patch has been removed and the second patch has been positioned on the patient as described above. The ECG signal can be measured with electronics components and electrodes, as described above.

A step 470 determines a second orientation of the electrode measurement axis on the patient. The second orientation of the electrode measurement axis may comprise orientation of an axis of a second set of electrodes, for example a second set of electrodes disposed along an axis of the second patch. The second orientation of the electrode measurement axis may correspond to one of the measurement axes of the 3D accelerometer, for example an X-axis of the accelerometer as described above. However, the second orientation of the electrode measurement axis can be aligned in relation to the axes of the accelerometer in many ways, for example at oblique angles, such that the alignment of the accelerometer with the second electrode measurement axis is known and the signal from the accelerometer can be used to determine the alignment of the electrode measurement axis.

A step 475 determines a second orientation of the ECG vector. The second orientation of the ECG vector can be determined in response to the polarity of the second measurement electrodes and second orientation of the electrode measurement axis, for example second measurement electrodes on the second adherent patch that extend along the electrode measurement axis of the second adherent patch.

A step 480 rotates a second ECG vector. The second ECG vector orientation of the second ECG vector can be used to rotate the second ECG vector onto the desired axis, for example the X-axis of the patient in response to the first orientation of the ECG vector and the accelerometer signal. For example, if the first measurement axis of the first ECG vector is rotated five degrees from the X-axis based on the accelerometer signal, the first ECG vector can be rotated by five degrees so as to align the first ECG vector with the X-axis of the patient, for example the horizontal axis of the patient.

A step 485 measures a second patient temperature. The second temperature of the patient can be measured with electronics of the adherent device, as described above.

A step 490 measures a second patient impedance. The second patient impedance may comprise a four pole impedance measurement, as described above. The second patient impedance can be used to determine respiration of the patient and/or hydration of the patient.

A step 495 repeats the above steps. The above steps can be repeated to provide longitudinal monitoring of the patient with differential measurement of patient status. The monitoring of the patient may comprise a comparison of baseline patient data with subsequent patient date.

Many of the steps of method 400 can be performed with the processor system, as described above.

It should be appreciated that the specific steps illustrated in FIG. 4A provides a particular method of monitoring a patient, according to an embodiment of the present invention. Other sequences of steps may also be performed according to alternative embodiments. For example, alternative embodiments of the present invention may perform the steps outlined above in a different order. Moreover, the individual steps illustrated in FIG. 4A may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A system for monitoring a patient, the system comprising:
    a first adherent device adapted to be adhered to a skin of a patient, the first adherent device having a first support with a first adhesive configured to adhere the first support to the skin, the first adherent device including first electrodes supported with the first support to couple to the skin of the patient, the first adherent device adapted to measure physiological parameters of the patient with the first electrodes when coupled to the skin of the patient during a first monitoring period, the first electrodes defining a first electrode axis;
    a second adherent device adapted to be adhered to the skin of the patient, the second adherent device having a second support with a second adhesive configured to adhere the second support to the skin, the second adherent device including second electrodes supported with the second support to couple to the skin of the patient, the second adherent device adapted to measure physiological parameters of the patient with the second electrodes when coupled to the skin of the patient during a second monitoring period subsequent the first monitoring period, the second electrodes define a second electrode axis;
    at least one accelerometer couplable to at least one of the first adherent device or the second adherent device and having a measurement axis aligned with the respective electrode axis, wherein the at least one accelerometer is adapted to determine an orientation of the respective electrode axis of the first electrodes or the second electrodes relative a reference axis of the patient when coupled to the first or second adherent device during the respective monitoring periods; and
    a processor system comprising a tangible medium configured to modify the measured physiological parameters based on the determined orientations of the first electrode axis or the second electrode axis such that errors in the physiological parameter measurements associated with changes in the orientation of the first and second adherent devices are reduced.

2. The system of claim 1, wherein the at least one accelerometer comprises a first accelerometer coupled to the first adherent device in a first predetermined orientation and a second accelerometer coupled to the second adherent device in a second predetermined orientation.

3. The system of claim 1 wherein the reference axis of the patient corresponds to a vertical axis of the patient that extends vertically when the patient is standing or sitting.

4. The system of claim 1, wherein one or both of the first and second monitoring period is 90 days or more.

5. The system of claim 1, further comprising:
    a remote server communicatively coupled with the intermediate device such that the remote server receives the physiological measurements from the intermediate device for physiological monitoring of the patient.

6. A system for monitoring a patient, the system comprising:
    a first adherent measurement device adapted to be adhered to a skin of a patient, the first adherent measurement device comprising a first support with a first adhesive configured to adhere the first support to a skin of the patient, the first adherent measurement device comprising a first accelerometer and a first at least two measurement electrodes, the first adherent device comprising first measurement circuitry configured to measure a first accelerometer signal with the accelerometer and a first electrocardiogram signal with the first at least two measurement electrodes during a first monitoring period;
    a second adherent measurement device adapted to be adhered to the skin of the patient, the second adherent measurement device comprising a second support with a second adhesive configured to adhere the second support to the skin, the second adherent measurement device comprising a second accelerometer and a second at least two measurement electrodes, the second accelerometer comprising second circuitry configured to measure a second accelerometer signal with the second accelerometer and a second electrocardiogram signal with the second at least two measurement electrodes during a second monitoring period subsequent the first monitoring period; and
    a processor system comprising a tangible medium configured to combine the first electrocardiogram signal with the second electrocardiogram signal in response to the first accelerometer signal and the second accelerometer signal, wherein the processor system is configured to determine an orientation of the first electrode measurement axis relative a reference axis of the patient in response to the first accelerometer signal and determine an orientation of the second electrode measurement axis relative the reference axis of the patient in response to the to the accelerometer signal, wherein the reference axis corresponds to a vertical axis of the patient that extends vertically along the patient when the patient is standing or sitting.

7. The system of claim 6 wherein the first accelerometer comprises a first accelerometer measurement axis and the first at least two electrodes are separated by a first distance to define a first electrode measurement axis, the first accelerometer measurement axis aligned with the first electrode measurement axis, and wherein the second accelerometer comprises a second accelerometer measurement axis and the second at least two electrodes are separated by a second distance to define a second electrode measurement axis, the second accelerometer measurement axis aligned with the second electrode measurement axis.

8. The system of claim 6 wherein the processor system comprises at least one processor supported by at least one of the first support or the second support, the at least one processor configured to combine the first electrocardiogram signal and the second electrocardiogram signal in response to the first accelerometer signal and the second accelerometer signal.

9. The system of claim 6 wherein the processor is configured to scale each electrocardiogram signal and sum the scaled electrocardiogram signals together to combine the electrocardiogram signals.

10. A method of monitoring a patient, the method comprising:
adhering a first adherent device to a skin of the patient, the adherent device comprising a first accelerometer and at least two physiological measurement electrodes, the at least two physiological measurement electrodes separated by a distance to define an electrode measurement axis;
a processor system receiving an accelerometer signal provided by the accelerometer of the first adherent device when the first adherent device is adhered to the patient;
the processor system determining a reference axis of the patient corresponding to a vertical axis that extends vertically along the patient when the patient is standing and determining an orientation of the electrode measurement axis of the first adherent device relative the reference axis in response to the accelerometer signal of the first adherent device;
the processor system receiving physiological parameters of the patient provided by with the at least two physiological measurement electrodes of the first adherent device when the first adherent device is coupled to the skin of the patient and the processor system modifying the physiological parameter measurements obtained from the first adherent device based on the determined orientation of the electrode measurement axis of the first adherent device;
adhering a second adherent device to a skin of the patient, the adherent device comprising the first accelerometer or a second accelerometer and at least two physiological measurement electrodes, the at least two physiological measurement electrodes separated by a distance to define an electrode measurement axis;
the processor system receiving an accelerometer signal provided by from the accelerometer of the second adherent device when the second adherent device is adhered to the patient;
the processor system determining an orientation of the electrode measurement axis of the second adherent device relative the reference axis of the patient in response to the accelerometer signal of the second adherent device;
removing the first adherent device from the patient; and
the processor system receiving physiological parameters of the patient provided by the at least two physiological measurement electrodes of the second adherent device and the processor system modifying the physiological parameter measurements obtained from the second adherent device based on the determined orientation of the electrode measurement axis of the second adherent device relative the reference axis of the patient such that differences in the measured physiological parameters associated with changes in the orientation of the first and second adherent devices are reduced.

11. The method of claim 10 wherein the first accelerometer or the first and second accelerometers each comprises at least one measurement axis sensitive to gravity aligned with the electrode measurement axis.

12. The method of claim 10 wherein the first accelerometer or the first and second accelerometers each comprises at least one accelerometer measurement axis sensitive to gravity, the at least one accelerometer measurement axis configured to extend substantially horizontally on the patient when the device is adhered to the patient.

13. The method of claim 10 wherein the accelerometer signal of the first accelerometer or of the first and second accelerometers corresponds to at least one accelerometer measurement vector in a direction along the at least one accelerometer measurement axis.

14. The method of claim 10 wherein the first accelerometer or the first and second accelerometers each comprises at least one accelerometer measurement axis sensitive to gravity and wherein the at least one accelerometer measurement axis is oriented with respect to the electrode measurement axis in a predetermined configuration.

15. The method of claim 10 wherein each of the first and second adherent devices comprises an adherent surface to adhere to a skin of the patient and wherein the electrode measurement axis extends along the adherent surface.

16. The method of claim 10 wherein the first accelerometer or the first and second accelerometers each comprises three axes, wherein a first axis and a second axis of the three axes extend along the measurement surface and a third axis of the three axes extends away from the measurement surface and the accelerometer measurement signal corresponds to three orthogonal measurement vectors, wherein each of the three orthogonal measurement vectors extends along one of the accelerometer measurement axes.

17. The method of claim 10 further comprising the processor system receiving an electrocardiogram signal sensed by the at least two measurement electrodes of each of the first and second adherent devices when coupled to the patient and modifying the electrocardiogram signal of the second adherent device in response to the accelerometer signal.

18. The method of claim 17 wherein modifying comprises rotating the electrocardiogram vector in response to the accelerometer signal to obtain a standard electrocardiogram vector.

19. The method of claim 18 wherein an amplitude and a direction of features of the electrocardiogram signal are modified to approximate a standard electrocardiogram vector.

20. The method of claim 10, further comprising:
an intermediate device wirelessly coupled with each of the first adherent device and second adherent device when coupled to the skin of the patient, and receiving physiological measurement from the at least two physiological measurement electrodes of each of the first adherent device and second adherent device.

21. The method of claim 20, further comprising:
a remote server communicatively coupled with the intermediate device such that the remote server receives the physiological measurements from the intermediate device for physiological monitoring of the patient.

22. The method of claim 21, wherein the remote server comprises a processor for modifying the physiological measurement data.

23. The method of claim 10, wherein the second adherent device is adhered before removal of the first adherent device.

24. The method of claim 10, wherein the second adherent device is adhered after removal of the first adherent device.

25. The method of claim 10, further comprising:
removing the accelerometer from the first adherent device and coupling the accelerometer to the second adherent device such that the first and second adherent devices utilize the same accelerometer.

* * * * *